(12) United States Patent
Roth

(10) Patent No.: US 7,876,423 B1
(45) Date of Patent: Jan. 25, 2011

(54) SIMULTANEOUS NONCONTACT PRECISION IMAGING OF MICROSTRUCTURAL AND THICKNESS VARIATION IN DIELECTRIC MATERIALS USING TERAHERTZ ENERGY

(75) Inventor: Donald J Roth, Rocky River, OH (US)

(73) Assignee: The United States of America as represented by the National Aeronautics and Space Administration, Washington, DC (US)

( * ) Notice: Subject to any disclaimer, the term of this patent is extended or adjusted under 35 U.S.C. 154(b) by 154 days.

(21) Appl. No.: 12/163,382

(22) Filed: Jun. 27, 2008

(51) Int. Cl.
*G01N 21/00* (2006.01)
*G01B 11/28* (2006.01)
(52) U.S. Cl. ........................ 356/27; 356/630
(58) Field of Classification Search ............... 356/497, 356/502, 630–636, 27–28.5; 73/655, 629, 73/622, 597, 593
See application file for complete search history.

(56) References Cited

U.S. PATENT DOCUMENTS

| | | | |
|---|---|---|---|
| 4,056,970 A * | 11/1977 | Sollish ........................ | 73/629 |
| 4,533,829 A | 8/1985 | Miceli et al. | |
| 4,563,898 A * | 1/1986 | Kanda et al. ................... | 73/606 |
| 5,307,680 A * | 5/1994 | Drescher-Krasicka ......... | 73/606 |
| 5,549,003 A * | 8/1996 | Drescher-Krasicka ......... | 73/606 |
| 5,623,145 A | 4/1997 | Nuss | |
| 5,710,430 A | 1/1998 | Nuss | |
| 5,883,720 A * | 3/1999 | Akiyama et al. ............. | 356/632 |
| 5,939,721 A | 8/1999 | Jacobsen et al. | |
| 5,974,886 A * | 11/1999 | Carroll et al. ................. | 73/598 |
| 6,495,833 B1 | 12/2002 | Alfano et al. | |
| 6,810,742 B2 * | 11/2004 | Sauerland ..................... | 73/597 |
| 6,828,558 B1 | 12/2004 | Arnone et al. | |
| 6,849,852 B2 | 2/2005 | Williamson | |
| 6,853,926 B2 | 2/2005 | Alfano et al. | |
| 7,038,208 B2 | 5/2006 | Alfano et al. | |
| 7,119,339 B2 | 10/2006 | Ferguson et al. | |
| 7,145,148 B2 | 12/2006 | Alfano et al. | |
| 7,174,037 B2 | 2/2007 | Arnone et al. | |

(Continued)

OTHER PUBLICATIONS

"Simultaneous Non-Contact Precision Measurement of Microstructural and Thickness Variation in Dielectric Materials Using Terahertz Energy" NASA TM-2008-2148997, Mar. 2008, 2008-214997, NASA STI, http://www.sti.nasa.gov, NASA Center for AeroSpace Information (CASI) 7115 Standard Drive, Hanover, MD 21076-1320.

(Continued)

*Primary Examiner*—Sang Nguyen
(74) *Attorney, Agent, or Firm*—Ruth H. Earp, III; Kenneth Mitchell

(57) ABSTRACT

A process for simultaneously measuring the velocity of terahertz electromagnetic radiation in a dielectric material sample without prior knowledge of the thickness of the sample and for measuring the thickness of a material sample using terahertz electromagnetic radiation in a material sample without prior knowledge of the velocity of the terahertz electromagnetic radiation in the sample is disclosed and claimed. The process evaluates, in a plurality of locations, the sample for microstructural variations and for thickness variations and maps the microstructural and thickness variations by location. A thin sheet of dielectric material may be used on top of the sample to create a dielectric mismatch. The approximate focal point of the radiation source (transceiver) is initially determined for good measurements.

20 Claims, 15 Drawing Sheets

U.S. PATENT DOCUMENTS

| | | | |
|---|---|---|---|
| 7,214,940 | B2 | 5/2007 | Cluff et al. |
| 2004/0026622 | A1 | 2/2004 | DiMarzio et al. |
| 2004/0095147 | A1 | 5/2004 | Cole |
| 2004/0113103 | A1 | 6/2004 | Zhilkov |
| 2007/0090294 | A1 | 4/2007 | Safai et al. |
| 2007/0145276 | A1 | 6/2007 | Zhang et al. |
| 2007/0228280 | A1 | 10/2007 | Mueller |
| 2007/0235658 | A1 | 10/2007 | Zimdars et al. |

OTHER PUBLICATIONS

Columbia Accident Investigation Board (CAIB) Report, vol. 1, Aug. 2003.

Generazio, E.R.. Roth, D.J., and Stang, D.B.: "Ultrasonic Imaging of Porosity Variations Produced During Sintering," J. Am. C'ertrm. Soc. vol. 72, No. 7, 1989.

Hu, B.B. and Nuss, M.C., "Imaging with terahertz waves," Opt. Lett., vol. 20, p. 1716 (1995).

Hsu. D.K.. et al.: Simultaneous determination of ultrasonic velocity, plate thickness i~nd wedge angle using one-sided contact measurements. NDT&E International 1994 vol. 27, No. 2, pp. 75-82.

Hull. D.R.; Kautz, H.E.; and Vary. A.: Measurement of Ultrasonic Velocity Using FS-Slope and Cross-Correlation Methods, Mater, Eval. vol. 43,. No. 11, 1985, pp. 1455-1460.

Mittleman, D.M., Jacobsen, R.H., and Nuss, M.C., "T-ray imaging," IEEE J.Sel.Top. Quant. Elec., vol. 2, p. 679 (1996).

Mittleman D.M., Gupta, M. Neelamani, R.G., Baraniuk, J.V., Rudd and Koch, M., "Recent advances in terahertz imaging," Appl. Physics. B vol. 68. pp. 1085-1094 (1999).

Piche, L.: Ultrasonic velocity measurement for the determinination of density in polyethylene. Polymer Engineering and Science, vol. 24, No. 17, Mid-Dec. 1984 oo 1354-1358.

Roth, D.J., Kiser, J.D., Swickard, S.M., Szatmary, S., and Kerwin, D. "Quantitative Mapping of Pore Fraction Variations in Silicon Nitride Using an Ultrasonic Contact Scan Technique," Research in Nondestructive Evaluation, vol. 6, No. 3, 1995.

Roth, D.J., Carney, D.V., Baaklini, G.Y., Bodis, James R., Rauser, Richard W., "A Novel Method for Nondestructive Characterization of Tubular and Curved Components," Materials Evaluation, vol. 56, No. 10, Sep. 1998, pp. 1053-1061.

Roth, D.J. and Farmer, D.A., "Thickness-Independent Ultrasonic Imaging Applied to Abrasive Cut-off Wheels: An Advanced Aerospace Materials Characterization Method for the Abrasives Industry: A NASA Lewis Research Center Technology Transfer Case History," Materials Evaluation, vol. 58, No. 4, Apr. 2000.

Roth, D.J. Hendricks, L., Whalen. M.F. and Martin, K: Commercial Implementation of Ultrasonic Velocity Imaging Methods via Cooperative Agreement Between NASA—Lewis Research Center and Sonix. Inc. NASA TM-107138, 1996.

Winfree, W.P. and Madaras, E.I., "Detection and Characterization of Flaws in Sprayed on Foam Insulation with Pulsed Terahertz Frequency Electromagnetic Waves," Proceedings Proceedings of the 41st AIAA/ASME/SAE/ASEE Joint Propulsion Conference & Exhibit, Tuscon. Arizona, Jul. 10-13, 2005.

Allan, H., Huang, F., Federici. J.F., Lan, A., and Grebel, H., "Characteristics of Nano-scale Composite Materials using THz spectroscopy," Proc. SPIE 5268, pp. 53-60, (2004).

Amone, D.D.; et al. Application of terahertz (THz) technology to medical imaging. In Proc. SPZE Ternhertz Spectroscopy. Applications II; International Society for Optical Engineering: Bellingham, WA, 1999; pp. 209-219.

Bashyam. M.: Thickness Compensation and Dynamic Range Improvetnent for Ultrasonic Imaging of Composite Materials. Proc. Of the 17th Annual Review of Progress in Qualitative Nondestructive Evaluation, La Jolla. CA, Jul. 15-20. 1090. vol. 10.4. Plenuni Press. 1901, pp. 1035-1042.

Bevington R.P. Data Reduction and Uncertainty Analysis for the Physical Sciences, Chapter 4, 1069. McGraw-Hill: New York, NY.

Jensen, A. and Ia Cour-Harbo, A.; Ripples in Mathematics. 157-160. (2001).Berlin: Springer, ISBN 3-540-41662-5.

Roth, D.J., Stang, D.B., Swickard, S.M., DeGuire, M.R., and Dolhert, L.E. "Review, Modeling and Statistical Analysis of Ultrasonic Velocity-Pore Fraction Relations in Polycrystalline Materials," Materials Evaluation, vol. 49, No. 7, Jul. 1991, pp. 883-888.

Roth, D.J., "Using a Single Transducer Ultrasonic Imaging Method to Eliminate the Effect of Thickness Variation in the Images of Ceramic and Composite Plates," Journal of Nondestructive Evaluation, vol. 16, No. 2, Jun. 1997.

Roth, D.J., Seebo, J.P. Trinh, L.B., Walker, J.L., Aldrin, J.C., "Signal processing approaches for terahertz data obtained from inspection of the shuttle external tank thermal protection system foam," Procceedings of the 33rd Annual Review of Progress in Quantitative Nondestructive Evaluation. Hilton Portland & Executive Tower Portland, Oregon Jul. 30-Aug. 4, 2006.

Dayal, V. "An Automated Simultaneous Measurement of Thickness and Wave Speed by Ultrasound," Experimental Mechanics, 32(3), pp. 197-202, 1992.

\* cited by examiner

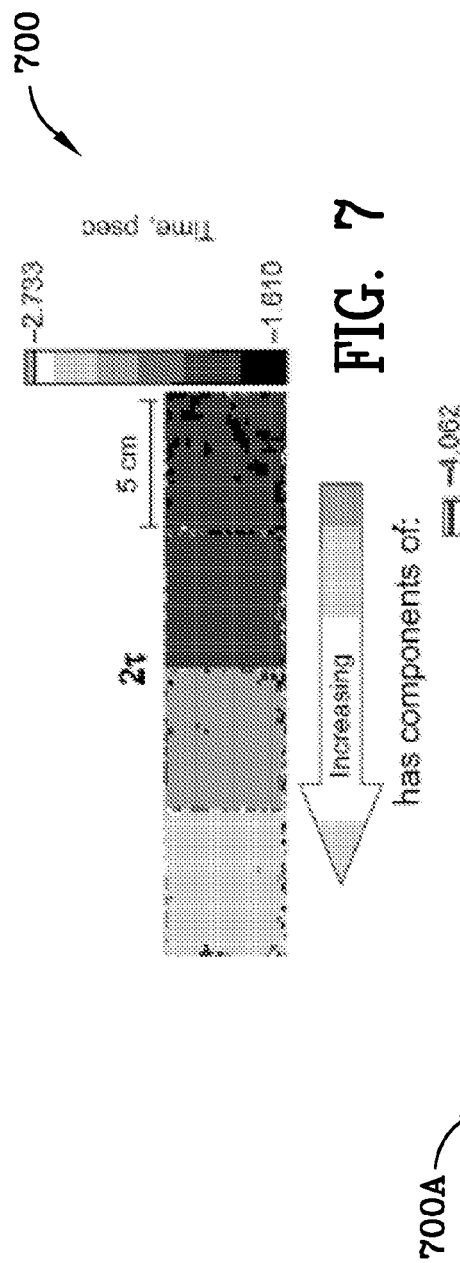

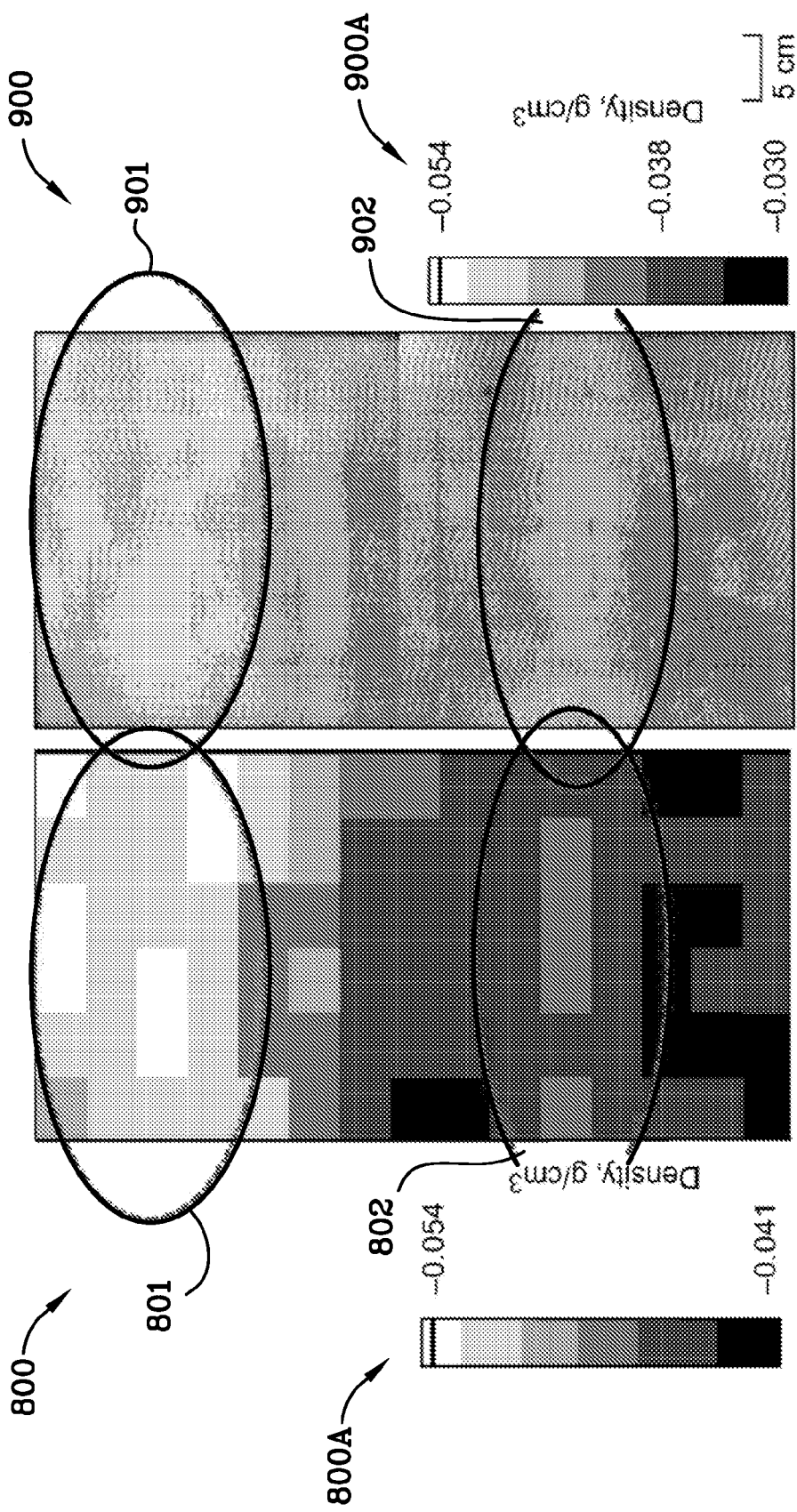

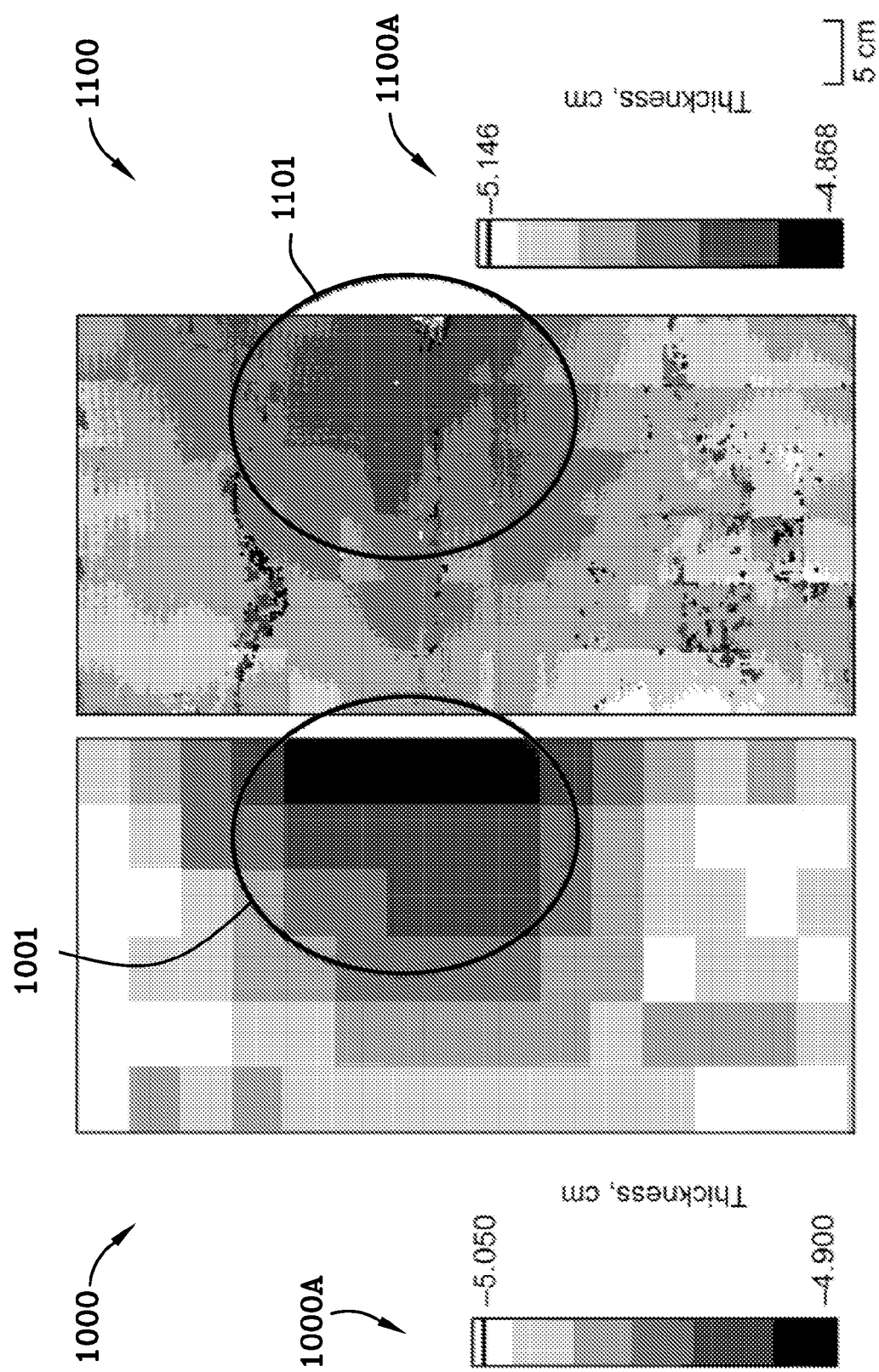

SIMULTANEOUS NONCONTACT PRECISION IMAGING OF MICROSTRUCTURAL AND THICKNESS VARIATION IN DIELECTRIC MATERIALS USING TERAHERTZ ENERGY

ORIGIN OF THE INVENTION

The invention described herein was made by an employee of the United States Government, and may be manufactured and used by the government for government purposes without the payment of any royalties therein and therefor.

FIELD OF THE INVENTION

As a result of Space Shuttle Columbia Accident Investigation Board recommendations, an aggressive program to eliminate all External Tank Thermal Protection System debris-shedding at the source was initiated. Terahertz c-scan imaging is an emerging and very effective nondestructive evaluation (NDE) technique used for dielectric materials analysis and quality control in the pharmaceutical, biomedical, security, materials characterization, and aerospace industries.

BACKGROUND OF THE INVENTION

Flaws present in the Space Shuttle external tank thermal protection system may play a role in foam release and are therefore important to detect and characterize prior to flight. The external tank configuration has sprayed-on foam insulation placed on top of the metal container and thus lends itself to terahertz inspection. Terahertz inspection has shown significant promise for detection of voids in the foam. Other potentially undesirable foam anomalies that have been identified by NASA include density variations and crushed foam. Velocity imaging can be used to identify density variations.

Terahertz waves are electromagnetic waves with wavelengths on the order of 200 to 1000 µm. Reflections occur to varying degrees at interfaces between materials with dissimilar dielectric properties (difference in indices of refraction). Metallic materials totally reflect terahertz waves while non-polar liquids, dielectric solids, and gases are at least partially transparent to terahertz energy. Continuous wave (narrowband) and pulsed (broadband) terahertz systems exist.

Several attempts to separate thickness and microstructural variation effects in ultrasonic images are noted in the literature. Several references showed single point (non-imaging) ultrasonic measurement methodology that accounted for thickness variation effects. See, Sollish. B. D., Ultrasonic Velocity and Thickness Gage, U.S. Pat. No. 4,056,970, Nov. 8. 1977. Hsu, D. K. et al., Simultaneous determination of ultrasonic velocity, plate thickness and wedge angle using one-sided contact measurements, NDT&E International 1994 vol. 27, no. 2, pp. 75-82 and Piche, L., Ultrasonic velocity measurement for the determination of density in polyethylene, Polymer Engineering and Science, vol. 24, no. 17, Mid-December 1984 pp. 1354-1358. Hsu et. al, 1994, simultaneously determined ultrasonic velocity, plate thickness and wedge angle. Piche, 1984, described a single point ultrasonic velocity measurement method using a reflector plate located behind the sample that does not require prior knowledge of sample thickness and lends itself to multiple measurements within a sample of nonuniform thickness. Several references proceeded to scale up and automate this ultrasonic method to obtain ultrasonic velocity images for plate and cylindrical samples of various materials of non-uniform thickness. See, for example, Dayal, V., "An Automated Simultaneous Measurement of Thickness and Wave Speed by Ultrasound," Experimental Mechanics, 32(3), pp. 197-202, 1992; and, Roth, D. J., Carney, D. V., Baaklini, G. Y., Bodis, James R., Rauser, Richard W., "A Novel Ultrasonic Method for Characterizing Microstructural Gradients in Tubular Structures," Materials Evaluation, Vol. 56, No. 9, September 1998, pp. 1053-1061.

A procedure utilized in ultrasonics and terahertz in which the substrate reflector plate time-of-flight scan with no sample present is subtracted from the same scan with the sample in place is useful to characterize microstructure and correct for setup nonuniformity i.e., levelness, but it will not separate thickness and microstructural effects.

Ultrasonic methods to simultaneously measure or characterize thickness and density (or variation as such) require water coupling. Additionally, the ultrasonic methods cannot be used for foam inspections due to the highly porous nature or highly cellular structure of foams. The terahertz method is totally non-contact, requires no coupling, and works in air.

SUMMARY OF THE INVENTION

Terahertz imaging is being used at NASA for nondestructive evaluation of the Space Shuttle external tank thermal protection system sprayed-on foam insulation (SOFI). The NASA Engineering and Safety Center tasked a technical team to develop improved inspection methods to characterize foam anomalies to help alleviate foam shedding on the space shuttle tanks. Foam density variation was identified as a potential problem in which thermal expansion mismatch between areas of different density could result in crack formation, subsequent foam shedding, and endangerment of the space shuttle orbiter. Prior to implementation of the method disclosed herein it was not possible to quantitatively measure density using a totally non-contact, non-water-coupled method. Generally, terahertz is used in the pulse-echo c-scan configuration to map variations in the peak amplitude of the echo off of the metal substrate (equivalent to the location of the back surface of the foam) that occur when scanning across a section of foam in order to detect voids, cracks, disbonds, and any sort of discontinuity. Traditional c-scan imaging scales the peak amplitude values (to an 8- or 16-bit gray or color scale) at each scan location to form an image.

Since the pulse-echo terahertz method results in a waveform with echos being received off of the front surface of a dielectric material and a metal (electrically-conducting) substrate that the dielectric material rests on, obtaining the time delay between front surface and substrate (with the sample present) echos is possible. Terahertz velocity is affected by variations in a volumetric microstructural property such as physical density and thereby once a relationship between the two variables is established, a non-contact precise measurement of density can be made using terahertz energy.

If the dielectric material has flat and parallel sides such that no thickness variation exists, the time delay between the front surface echo and substrate echo with the sample present will be indicative of only microstructural variation. By obtaining the relationship between velocity and a microstructure property, such as density, using a series of samples of different density, one can then predict the density of the material and subsequently map density variations within the material using the established relation between velocity and density.

A pulse-echo terahertz velocity measurement is made by sending terahertz energy via a transceiver (device that has both a transmitter and a receiver) into and through a dielectric (insulating) material (such as the shuttle external tank thermal protection system sprayed on insulating foam) backed by a metallic (electrically-conducting) plate that reflects the terahertz energy back to the transceiver. The terahertz transceiver is separated from the dielectric sample by an air path. Velocity (V) values are calculated using the time delay between the front surface echo (FS) and substrate/reflector plate echo (BS). With a dielectric sample present between the transceiver and the reflector plate, the pulse that travels from the transceiver through the sample to the reflector plate (equivalent to the sample back surface position) and back to the transceiver is labeled BS and will be observed at time t'. Thus two "echos," FS and BS, can have their peak positions in time measured and the time difference or time delay between them is determined. Alternatively, the entire echos may be cross-correlated to obtain the precise time delay between them. If thickness is non-variable in the sample, the time-of-flight and/or velocity measured will be indicative only of the microstructure. The FS echo may require specialized signal processing to denoise and amplify it.

A process for measuring the velocity of terahertz electromagnetic radiation in a material sample without prior knowledge of the thickness of said sample is disclosed and claimed. Terahertz electromagnetic radiation is produced by a source (transceiver) spaced apart from the substrate and propagated at the speed of light, c, in a medium located between the source (transceiver) and the substrate. The process for measuring the velocity (independently of thickness) includes the following steps: emitting terahertz electromagnetic radiation from the source; measuring the travel time of the terahertz electromagnetic radiation to and from the substrate without the sample present, t" (t-double prime); placing the sample on the substrate; measuring the travel time of the terahertz electromagnetic radiation to and from the substrate with the sample present, t' (t-prime); subtracting t" from t' to determine the transmission time difference with the sample present and without the sample present, $\Delta t$; measuring the travel time of the terahertz electromagnetic radiation to and from the sample, $2t_1$; time determining the difference between the FS echo and the BS echo, $2\tau$; dividing $\Delta t$ by $2\tau$ and determining the quotient; and, subtracting the quotient from 1 to obtain a factor; multiplying the factor by, c, to determine the velocity of the terahertz electromagnetic radiation in the sample. The further step of determining the microstructural variation of the sample according to an algorithm is performed to determine, for instance, the density of the foam. The step of determining the microstructual variation of the sample includes determining the density of the material. The sample may be foam or another dielectric such as silicon nitride. The radiation may be pulsed or it may be continuous.

If the surface to be evaluated is large, then mapping microstructural variations in a plurality of locations is performed. When the terahertz electromagnetic radiation reaches the front surface of the sample, the echo therefrom may not be very prominent if the dielectric mismatch between the air path and the sample and the dielectric itself is not substantial enough. The step of measuring the travel time of the terahertz electromagnetic radiation to and from the sample, $2t_1$ optionally includes placing a sheet of plastic transparent paper onto the sample to create an adequate dielectric mismatch between the air and the sample. The plastic transparent paper is thin, for example, it may be approximately 250 µm thick or less. The plastic paper does not have to be transparent. It is necessary to know, a priori, the approximate distance between the transceiver and the front surface of the sample. As used herein "a priori" means before knowledge of the exact distances between the transceiver and the front surface of the sample.

The front surface echo (FS) from the dielectric material (sample) may be of very low signal-to-noise ratio (SNR) depending on the dielectric match between air and the sample. If a good dielectric match exists, much of the terahertz energy will be transmitted into the sample. Additionally, the focal plane sensitivity of the terahertz method disclosed herein, may, for samples of nonuniform thickness, result in the front surface echo (FS) too far out of focus and thus reduce the signal to noise ratio (SNR) even further, thus limiting the thickness variation over which the method can be used. The approximate time location of FS must be known "a priori" and the wavetrain examined manually through observation of the signal on an oscilloscope trace to determine what special post-processing needs to be applied. In this way amplification and denoising the front surface signal (FS) can be achieved. Therefore, the further process steps of controlling, approximately, the spacing between the source (transceiver) and the substrate and the spacing between the source and the front surface are usually performed preliminarily if necessary. It is also necessary to know the approximate distance between the transceiver and the metal substrate.

The step of controlling the spacing between the source and the substrate includes determining, initially, the approximate time location of the sample from the terahertz radiation source as well as the approximate time location of the substrate from the terahertz radiation source.

Identical scan data may be used for measuring the thickness of a material sample using terahertz electromagnetic radiation in a material sample without prior knowledge of the velocity of the terahertz electromagnetic radiation in the sample. In other words density and thickness can be obtained from the same scan data. The terahertz electromagnetic radiation is produced by a source (transceiver) spaced apart from the substrate and propagated at the speed of light, c, in a medium (usually air) located between the source and the substrate. The steps in the process include: emitting pulsed (or continuous) terahertz electromagnetic radiation from the source; measuring the travel time of the terahertz electromagnetic radiation to and from the substrate without the sample present, t" (t-double prime); placing the sample on the substrate; measuring the travel time of the terahertz electromagnetic radiation to and from the substrate with the sample present, t' (t-prime); subtracting t" from t' to determine the transmission time difference with the sample present and without the sample present, $\Delta t$; measuring the travel time of the terahertz electromagnetic radiation to and from the sample, $2t_1$; determining the time difference between the FS echo and the BS echo, $2\tau$; subtracting $\Delta t$ from $2\tau$ to obtain a subtraction result; dividing the subtraction result by 2 to obtain a quotient; and, multiplying the quotient by, c, to obtain the thickness of the sample. Additionally, the method for determining thickness may include evaluating, in a plurality of locations, the sample for thickness variations and mapping the thickness variations by location.

The inventor discloses and claims herein a process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample. The pulsed terahertz electromagnetic radiation is produced by a source spaced apart from the sample under test and propagated at the speed of light, c, in a medium located between the source and the sample. The medium is typically air. The process includes the steps of: emitting (pulsed or continuous) terahertz electromagnetic radiation from the source; measuring the travel time of the terahertz electromagnetic radiation to and from the substrate without the sample present, t" (t-double prime); placing the sample on the substrate; measuring the travel time of the terahertz electromagnetic radiation to and from the substrate with the sample present, t' (t-prime); subtracting t" from t' to determine the transmission time difference with the sample present and without the sample present, $\Delta t$; measuring the travel time of the terahertz electromagnetic radiation to and from the sample, $2t_1$; determining the time difference between the FS echo and the BS echo, $2\tau$; dividing $\Delta t$ by $2\tau$ and determining the quotient; subtracting the quotient from 1 to obtain a factor; multiplying the factor by, c, to determine the velocity of the terahertz electromagnetic radiation in the sample; subtracting $\Delta t$ from $2\tau$ to obtain a subtraction result; dividing the subtraction result by 2 to obtain a quotient; multiplying the quotient by, c, to obtain the thickness of the sample; and, evaluating, in a plurality of locations, the sample for microstructural variations and for thickness variations, and mapping the microstructural and thickness variations by location.

Another process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample is disclosed herein which comprises the steps of: merging the FS, BS, and M" scan data sets into a fused data file; producing a "fused" waveform; calculating time delays between FS, BS and M" echos; determining precision thickness-independent velocity images that map microstructure; and, determining precision microstructure-independent thickness images that map thickness. The steps of calculating the time delays and determining precision thickness and microstructure are performed by cross-correlating FS and BS signals (echos) and by cross correlating BS and M" signals (echos). The steps of calculating the time delays and determining precision thickness and microstructure may also be performed by precisely identifying peaks of FS, BS and M". Where FS is believed to vary across a sample, an additional step of processing and gating the FS signal prior to merging the data into a fused data file is performed. Optionally, the step of amplifying the processed FS signal prior to merging the data into a fused data file is performed. To obtain a good dielectric mismatch between the sample and the air, the step of applying a dielectric sheet on the FS, followed by gating and processing the FS signal prior to merging the data into a fused data file is performed.

The methodology disclosed herein has applicability to all dielectric materials where non-contact, non-water-immersion precision determination of microstructural (density) variation is required. It can be used for precision density mapping in dielectric ceramic materials, other types of foam, and dielectric composite materials.

C-scan imaging involves mapping variations in the time-of-flight of a terahertz echo peak, or mapping the time delay between front surface and substrate (with the sample present) echos (FS, BS). The novel implementation described herein concerns itself more with mapping thickness or global microstructural variation (such as physical density variation) as opposed to discrete flaw detection. Time delay between the front surface echo (FS) and substrate echo (BS) (with the sample present) is directly affected by thickness variation (d) and terahertz velocity in the material (V). Terahertz velocity is affected by variations in a volumetric microstructural property such as physical density.

The terahertz method of inspecting metal reflector-backed dielectric materials provides velocity images free of thickness variation effects, i.e. thickness-independent. Additionally, the same methodology can be slightly manipulated to obtain thickness images free of microstructural variation effects, i.e. microstructure-independent. In simple terms thickness can be measured without knowing velocity and density or velocity can be measured without knowing thickness. A pulse-echo terahertz velocity measurement is made by sending terahertz energy via a transceiver (device that has both a transmitter and a receiver) into and through a dielectric (insulating) material (such as the shuttle external tank thermal protection system sprayed on insulating foam) backed by a metallic (electrically-conducting) plate that reflects the terahertz energy back to the transceiver. The terahertz transceiver is separated from the dielectric sample by an air path. Velocity (V) values are calculated using the time delay ($2\tau$) between the front surface echo (FS) and substrate reflection (BS) (with sample present). The novel pulse-echo method described herein for measuring velocity in a material sample uses echos off of the reflector plate without the sample present as well as the FS and BS echos with the sample present.

With a dielectric sample present between the transceiver and the reflector plate, the pulse that travels from the transceiver through the sample to the reflector plate (equivalent to the sample back surface position) and back to the transceiver is labeled BS and will be observed at time t'. Placing a dielectric sample in between the terahertz transceiver and the reflector plate slows down the terahertz pulse as compared to its travel time in air. Thus, with the sample removed, the pulse that travels from the transceiver to the reflector plate and back to the transceiver is labeled M" and will be observed at an earlier time t". For certain materials such as foams, by appropriate manipulations and substitutions of equations, the acquisition of scans of the FS, BS, and M" (echo off reflector without sample present) echos, the conditioning of the FS echo thru amplification, DC subtraction, and software denoising, the fusing (combining) of FS, BS, and M" data sets (through use of software), and the subsequent calculation of time delays between echos, precision thickness-independent velocity images (that map microstructure) and microstructure-independent thickness images (that map thickness) (through software) are obtained.

The use of terahertz energy to simultaneously determine density and thickness variation in dielectric materials is new. The method is totally non-contact, very precise, and involves no fluid immersion.

Prior to implementation of this method, it was not possible to separate out effects of thickness and microstructural variation in time-of-flight images in totally non-contact, non-water-immersion fashion. No attempts to separate thickness and microstructural effects in terahertz time-of-flight images were noted in the literature. Ultrasonic methods to simultaneously measure or characterize thickness and density (or variation as such) require water coupling. Additionally, the ultrasonic methods cannot be used for foam inspections due to the highly porous nature or highly cellular structure of foams. The terahertz method is totally non-contact, requires no coupling, and works in air.

It is an object of the invention to simultaneously: (1) measure the velocity of terahertz electromagnetic radiation in a material sample without prior knowledge of the thickness of the sample; and, (2) measure the thickness of a material sample using terahertz electromagnetic radiation in a material sample without prior knowledge of the velocity of the terahertz electromagnetic radiation in the sample.

It is an object of the invention to provide a non-contact single-sided terahertz electromagnetic measurement and imaging method that simultaneously characterizes microstructural (for example, spatially-lateral density) and thickness variation in dielectric (insulating) materials.

It is an object of the present invention to provide a non-contact single-sided terahertz electromagnetic measurement and imaging method that simultaneously characterizes microstructural and thickness variation in dielectric (insulating) materials.

It is an object of the present invention to provide an inspection method for current and future thermal protection systems and for other dielectric material inspection applications where microstructural and thickness variation require precision mapping.

It is an object of the present invention to provide an inspection method which allows the separation of time-of-flight variations into its microstructural and thickness components.

It is an object of the present invention to provide simultaneous noncontact precision imaging of microstructural and thickness variation in dielectric materials using terahertz energy.

It is an object of the present invention to provide simultaneous noncontact precision imaging of microstructural and thickness variation in dielectric materials using terahertz energy using fused waveforms of terahertz energy from a fused data files produced by merging the FS, BS, and M" scan data sets for a set of foam blocks.

These and other objects will be better understood when reference is made to the drawings, the description of the invention and claims which follow hereinbelow.

BRIEF DESCRIPTION OF THE DRAWINGS

FIG. 7 illustrates a composite image of scans of the foam block sample set of FIG. 6 indicating $2\tau$ values of the foam blocks according to the methodology of the invention.

FIG. 7A illustrates an image of scans of the foam block sample set of FIG. 6 indicating thickness variations according to the methodology of the invention.

FIG. 7B illustrates an image of scans of the foam block sample set of FIG. 6 indicating density variations according to the methodology of the invention.

FIG. 8 illustrates a physically-measured density map in grams per cubic centimeter for a 6 by 15 set of foam blocks.

FIG. 8A illustrates the density by shade of gray in grams per cubic centimeter for the physically-measured density map shown in FIG. 8.

FIG. 9 illustrates a terahertz density map in grams per cubic centimeter for the 6 by 15 set of foam blocks of FIG. 8 derived from the velocity variations (determined independently of thickness) according to the methodology of the invention using the relationship between terahertz velocity and density for foam shown in FIG. 2.

FIG. 9A illustrates the density by shade of gray in grams per cubic centimeter for the terahertz density map of FIG. 9.

FIG. 10 illustrates a hand-measured thickness map in centimeters for the 6 by 15 set of foam blocks.

FIG. 10A illustrates the thickness by shades of gray indicated in centimeters for the thickness map of FIG. 10.

FIG. 11 illustrates a terahertz thickness map for the 6 by 15 set of foam blocks (determined independently of velocity) according to the methodology of the invention.

FIG. 11A illustrates the thickness by shade of gray in centimeters for the terahertz thickness map of FIG. 11.

DESCRIPTION OF THE INVENTION

Figure 1:
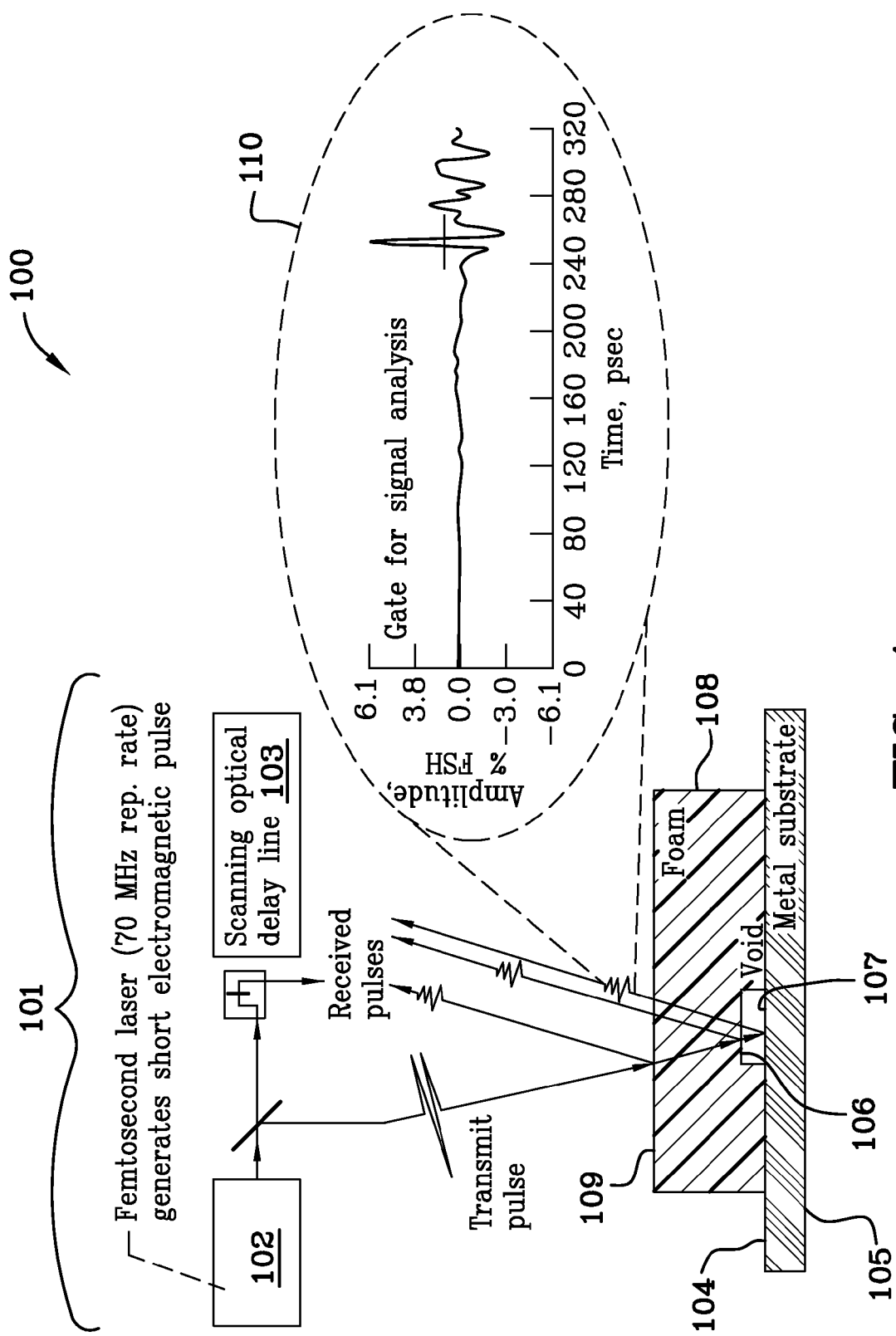
FIG. 1 is a schematic diagram of the reflection-mode terahertz methodology illustrating reflections received from the various interfaces and as an example of gating of the reflected signals.

FIG. 1 is a schematic diagram 100 of the reflection-mode terahertz methodology illustrating reflections received off of the various interfaces and gating of the reflected signal. A transceiver 101 includes a femtosecond laser (70 MHZ rep. rate) 102 which generates short terahertz electromagnetic pulses and a receiver 103. Reflections will be received from the various interfaces 109, 104. Reflection from the metal substrate 104 will be the strongest. The horizontal dotted line from the echo shows a time gate 110 typically used during signal processing. The back surface 105 of the metal substrate is illustrated as is the beginning of the void 106 in the foam, silicon nitride or other dielectric 108. The void in this example terminates 107 at the front surface of the metal substrate 104. The front surface of the foam, silicon nitride or other dielectric 109 is illustrated in FIG. 1 as is a graphical depiction of a gate 110 for signal analysis.

Terahertz imaging is being used at NASA for nondestructive evaluation of the Space Shuttle external tank thermal protection system sprayed-on foam insulation (SOFI). Generally, the terahertz method is used in the pulse-echo c-scan configuration to map variations in the peak amplitude of the echo off of the metal substrate after it has traveled through the foam. Traditional c-scan imaging scales the peak amplitude values (to an 8- or 16-bit gray or color scale) at each scan location to form an image.

An additional implementation of pulse-echo c-scan imaging involves mapping variations in the time-of-flight of a terahertz echo peak, or mapping the time delay between front surface and substrate (with the sample present) echos (FS, BS). This implementation concerns itself more with mapping thickness or global microstructural variation (such as physical density variation) as opposed to discrete flaw detection. Time delay (with the sample present $2\tau$) between the front surface echo (FS) and substrate echo (BS) is directly affected by thickness variation and terahertz velocity in the material according. See, FIG. 3. Here the designations ($2\tau$) and ($2d$) (versus t and d) are used since the ultrasonic echo travels through the material thickness in the pulse-echo mode.

Figure 2:
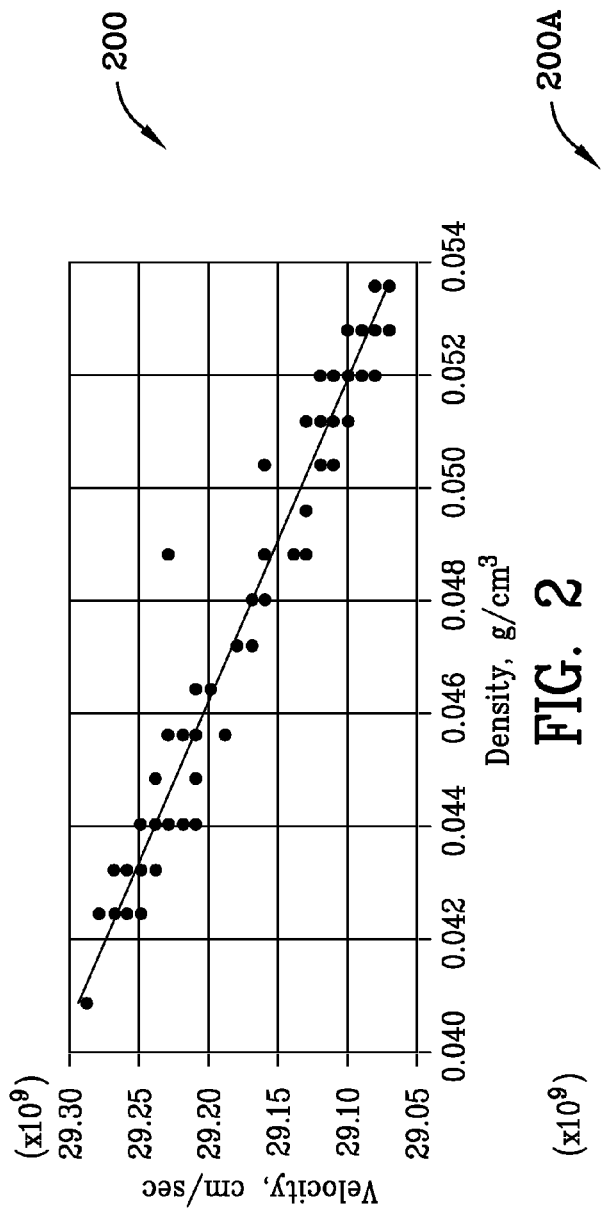
FIG. 2 is a plot of velocity versus density for foam.

Terahertz velocity is affected by variations in a volumetric microstructural property such as physical density as illustrated in FIG. 2, similar to the way ultrasonic velocity responds to microstructural variation.

Determining the relationship between velocity and density allows density maps to be obtained from velocity maps as set forth herein. Spatial variations in part thickness and/or spatially-lateral microstructural character will result in variations in maps of $2\tau$. Analagous to a complex number having real and imaginary parts, $2\tau$ images can be thought of as having thickness and microstructural components if both thickness and microstructural variation are present.

A terahertz method which allows the separation of time-of-flight variations into its microstructural and thickness components is disclosed herein. This method is important because it determines the extent of microstructural variation in a part that also has thickness variation. Additionally, it provides a non-contact method for mapping thickness and/or density.

Figure 2A:
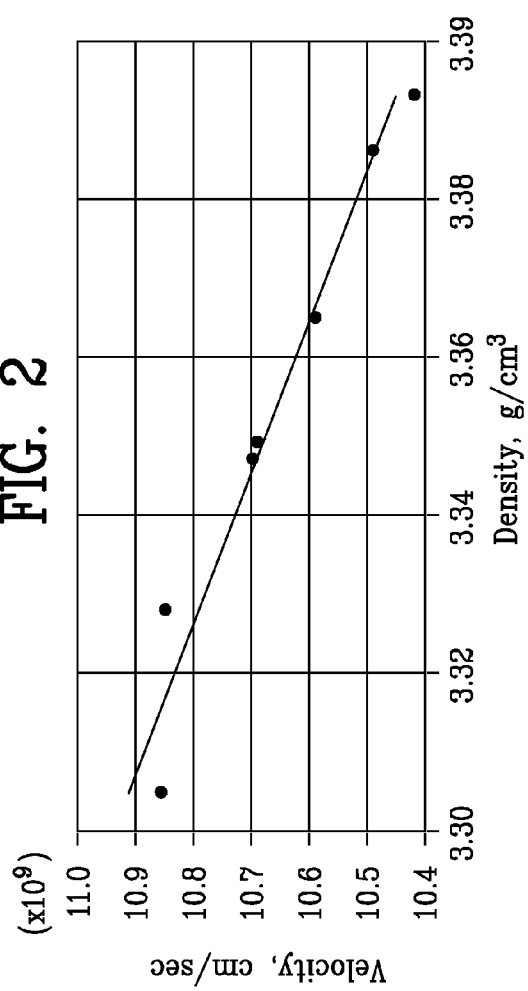
FIG. 2A is a plot of velocity versus density for silicon nitride.

FIG. 2 is a plot 200 of terahertz electromagnetic radiation velocity versus density for sprayed on foam. This enables the conversion of a given velocity into a respective density. FIG. 2A is a plot 200A of terahertz electromagnetic velocity versus density for silicon nitride.

Figure 3:
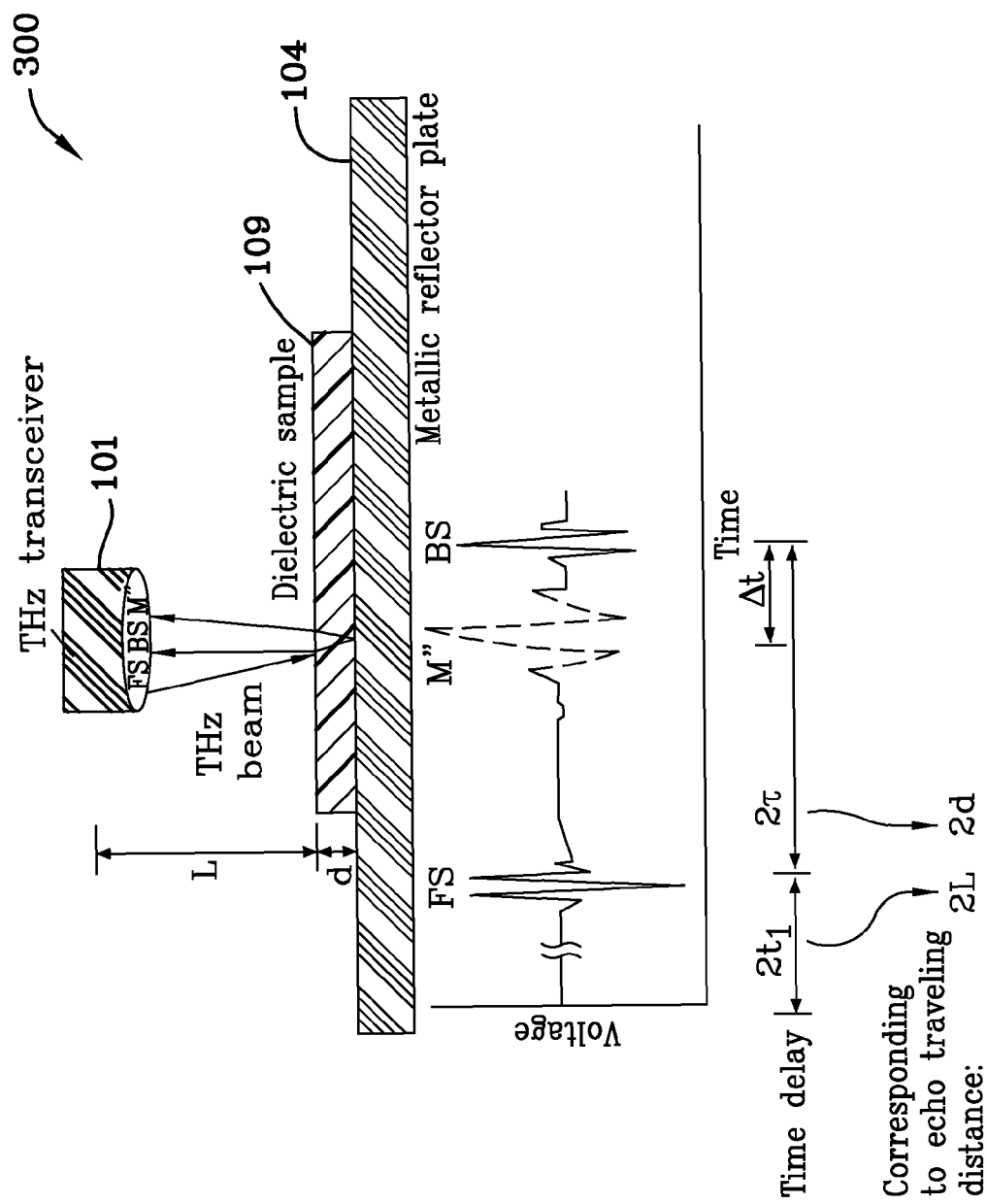
FIG. 3 illustrates a schematic of the pulse-echo terahertz testing method and resulting waveforms, including BS (time to and from the back surface of the dielectric sample), FS (time to and from the front surface of dielectric sample), L (distance between transceiver and sample), M"(pulse that travels from the transceiver to the reflector plate and back to the transceiver), d (sample thickness), t' (t-prime) (travel time of the terahertz electromagnetic radiation to and from the substrate with the sample present, equal to $2t_1$ plus $2\tau$), t"(t-double prime) (travel time of the terahertz electromagnetic radiation to and from the substrate without the sample present), $\Delta t$–(transmission time difference (t' minus t") with the sample present and without the sample present), $2t_1$ (travel time of the terahertz electromagnetic radiation to and from the front surface of the sample) and $2\tau$ (time difference between the FS echo and the BS echo).

FIG. 3 illustrates a schematic 300 of the pulse-echo terahertz testing method and resulting waveforms (output voltages), including: BS (time to and from the back surface of dielectric sample); FS (time to and from the front surface of the dielectric sample); L (distance between transceiver and sample); M" (pulse that travels from the transceiver to the reflector plate and back to the transceiver), d (sample thickness), t' (t-prime) (travel time of the terahertz electromagnetic radiation to and from the substrate with the sample present, equal to ($2t_1$) plus ($2\tau$); t" (t-double prime) (travel time of the terahertz electromagnetic radiation to and from the substrate without the sample present), $\Delta t$ transmission time difference (t' minus t") with the sample present and without the sample present; $2t_1$ (travel time of the terahertz electromagnetic radiation to and from the front surface of the sample); and, $2\tau$ (time difference between the FS echo and the BS echo).

As stated previously, the terahertz method of inspecting metal reflector-backed dielectric materials is utilized to simultaneously provide thickness-independent velocity (free of thickness effects) and microstructure-independent thickness (free of microstructure effects) images. A pulse-echo terahertz velocity measurement is made by sending terahertz energy via a transceiver (device that has both a transmitter and a receiver) into and through a dielectric (insulating) material backed by a plate (electrically-conducting, generally metallic) that reflects the terahertz energy back to the transceiver. The terahertz transceiver is separated from the dielectric sample by an air path.

The novel pulse-echo method described herein for measuring velocity in a material sample uses echoes off of the reflector plate with (BS) and without the sample present (M"), as well as using the echo (FS) off of the sample front surface. The following steps illustrate how velocity (V) in a sample of thickness (d) is determined without prior knowledge of thickness. With a dielectric sample present between the transceiver and the reflector plate, the pulse that travels from the transceiver through the sample to the reflector plate (equivalent to the sample back surface position) and back to the transceiver is labeled BS and will be observed at time t' where: t'($2t_1+2\tau$)

Referring to FIG. 3, the pulse-echo terahertz testing and resulting waveforms of FS and BS occur with the sample present. M" occurs without the sample present. ($2t_1$) and ($2\tau$) are the pulse-echo time delays of the terahertz pulse from the transceiver to the sample front surface and from the sample front surface to the substrate with the sample present.

Placing a dielectric sample in between the terahertz transceiver and the reflector plate slows down the terahertz pulse as compared to its travel time in air. Thus, with the sample removed, the pulse that travels from the transceiver to the reflector plate (metal substrate) 104 and back to the transceiver is labeled and will be observed at an earlier time t" where:

$$t''=(2t_1+2d/c))$$

where, c, is the velocity of terahertz energy in air and, d, is the air gap equal to the sample thickness.

The velocity of light at standard temperature and pressure was used for c in this investigation and is equal to 0.02997055434 cm/psec. Subtracting the time t" measured without the sample from the time measured with the sample, t', yields $\Delta t$, follows:

$$\Delta t = t' - t'' = (2\tau - 2d/c)$$

The thickness (d) of the sample can be determined in the pulse-echo configuration from: $2d=(2\tau)V$ which is simply velocity times time through the sample in both the forward and reverse directions. Solving for "d" and rearranging yields an expression for the velocity:

$$V = c(1 - \Delta t/2\tau)$$

As seen from the equation for velocity, sample thickness (d) is not a variable in the equation. Thus, this method does not require prior knowledge of sample thickness. If extended to multiple measurements across the sample (imaging), sample thickness variation effects are eliminated in the image allowing a true picture of microstructural variation for types of microstructural variation (such as density variation) that correlate with and will be revealed by velocity variation. For conventional time-of-flight imaging which does not separate velocity, V, and thickness, d, any thickness variation effects would corrupt the evaluation of microstructural variation (determined from velocity, V). Thus the new methodology allows true characterization of microstructural variation (i.e., density variation) in a material structure that is also nonuniformly thick.

The derived equation, namely, $V = c(1 - \Delta t/2\tau)$, illustrates how the terahertz velocity in a dielectric material will be reduced fractionally from that in air by the factor:

$$(1 - \Delta t/2\tau).$$

Further, rearranging $\Delta t = t' - t'' = (2\tau - 2d/c)$, to solve for sample thickness, d, yields:

$$d = c(2\tau - \Delta t)/2$$

which allows the calculation of absolute material thickness without prior knowledge of velocity. If extended to multiple measurements across the sample (imaging), sample microstructure variation effects are eliminated in the image allowing a true mapping of thickness variation. For conventional thickness mapping, microstructure variation effects would corrupt the evaluation of thickness variation.

Thus, the new methodology allows true characterization of thickness variation in a material structure that is of nonuniform microstructure. A key point of the methodologies disclosed and claimed herein is that both thickness-independent velocity and microstructure-independent thickness images can be derived from the same set of scan information.

In practice $2\tau$ is experimentally obtained from the pulse-echo time delay between the first front surface echo (FS) and substrate echo (BS) with the sample present. Either the time difference from FS peak location to BS peak location or cross-correlation of the waveforms of the two echoes can be used to obtain the $2\tau$ time delay. $\Delta t$ is the pulse-echo time difference between the echos off the reflector plate with (BS) and without (M") the sample present, respectively.

In fact, after the shuttle flight STS-114, the ability to nondestructively detect crushed foam became a significant priority. The microstructure-independent thickness mapping method can be used to identify and quantify areas of crushed (pushed-in) foam and precisely map thickness. The thickness-independent velocity method can be used to identify and quantify density variations in foam and other materials. It is worth noting that the previously-discussed ultrasonic methods for thickness-independent velocity and microstructure-independent thickness require water coupling while no such coupling is needed for terahertz methods. The latter fact makes the terahertz method much more practical than the ultrasonic method for dielectric materials.

Figure 3A:
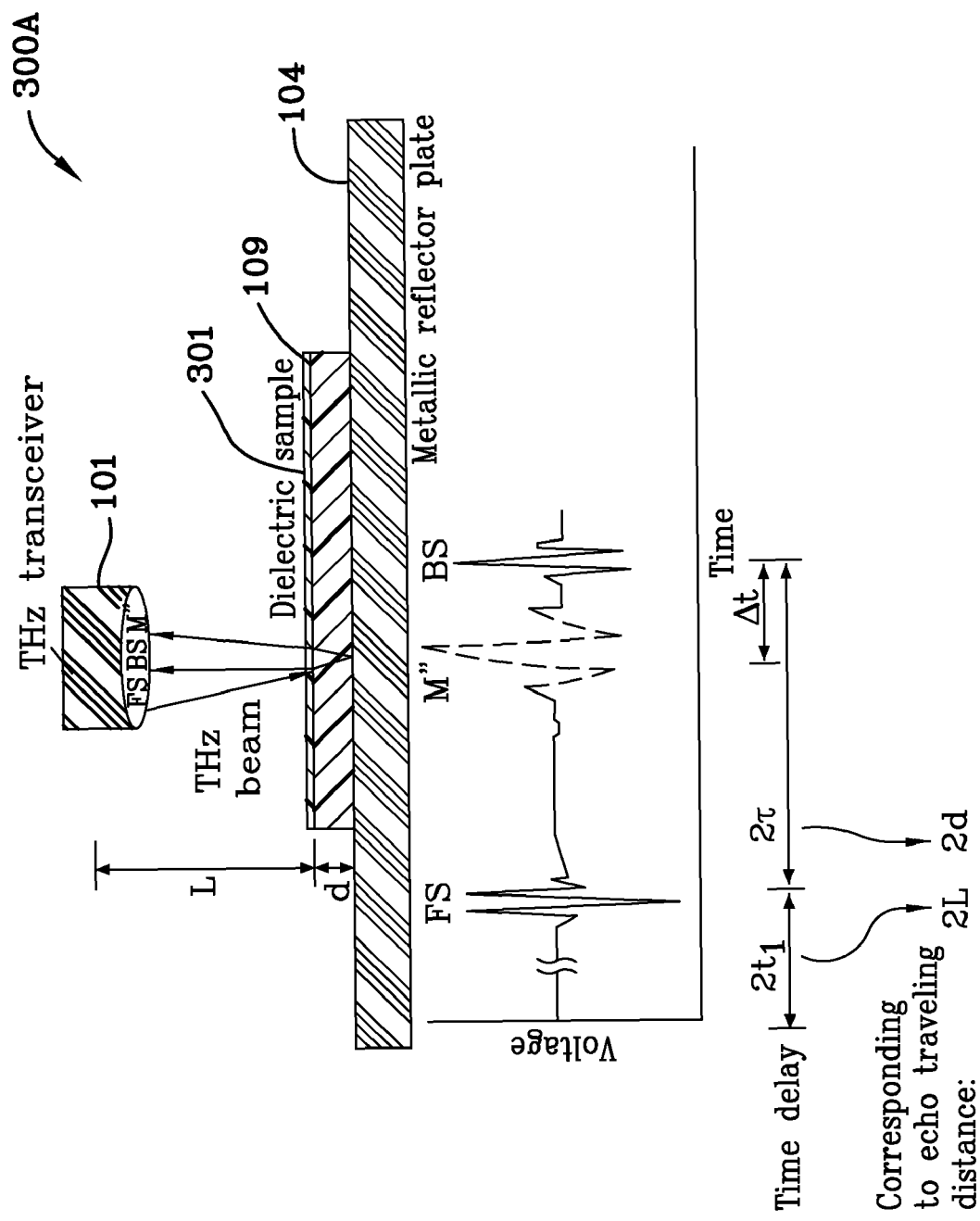
FIG. 3A illustrates a schematic similar to that illustrated in FIG. 3 with an additional thin dielectric material placed over the dielectric sample to create a dielectric mismatch.

The front surface echo (FS) from the dielectric material may be of very low signal-to-noise ratio (SNR) depending on the dielectric match between air and the sample. FIG. 3A illustrates a schematic similar to that illustrated in FIG. 3 with an additional thin dielectric material 301 placed over the dielectric sample to create a dielectric mismatch. If a good dielectric match exists, much of the terahertz energy will be transmitted into the sample and this presents somewhat of a problem. Additionally, the focal plane sensitivity of the terahertz method for samples of nonuniform thickness may result in the FS echo too far out of focus and thus reduce the signal to noise ratio (SNR) even further, thus limiting the thickness variation over which the method can be used. The approximate time location of the front surface echo (FS) off the dielectric sample must be known "a priori" and the wavetrain examined manually by an oscilloscope to determine special post-processing needs for amplification and denoising the front surface echo (FS). For the space shuttle external foam, the FS echo can be as small as 1/100th the amplitude of the BS (back surface of the sample) echo. This requires signal processing/conditioning steps of denoising and/or low-pass (smoothing) filtering followed by amplification (software gain) at the time location(s) of the FS echo to clearly separate the FS echo from baseline noise.

As stated above, to create a better dielectric mismatch situation in which more of the terahertz energy is reflected back to the receiving system while an ample amount is still transmitted into the sample, a sheet of very thin (250 µm) plastic transparency paper 301 can be placed onto the sample. See, FIG. 3A. This method can be used to locate the front surface echo (FS) locations prior to scanning, or in situations where it can be tolerated during actual scanning, will provide front surface echos having much greater signal to noise ratios. Also, knowledge of the distance between scanner head and sample top surface, velocity of terahertz in air (speed of light), and any post- or pre-trigger delays should allow calculation of approximate front surface echo time location(s).

Figure 4:
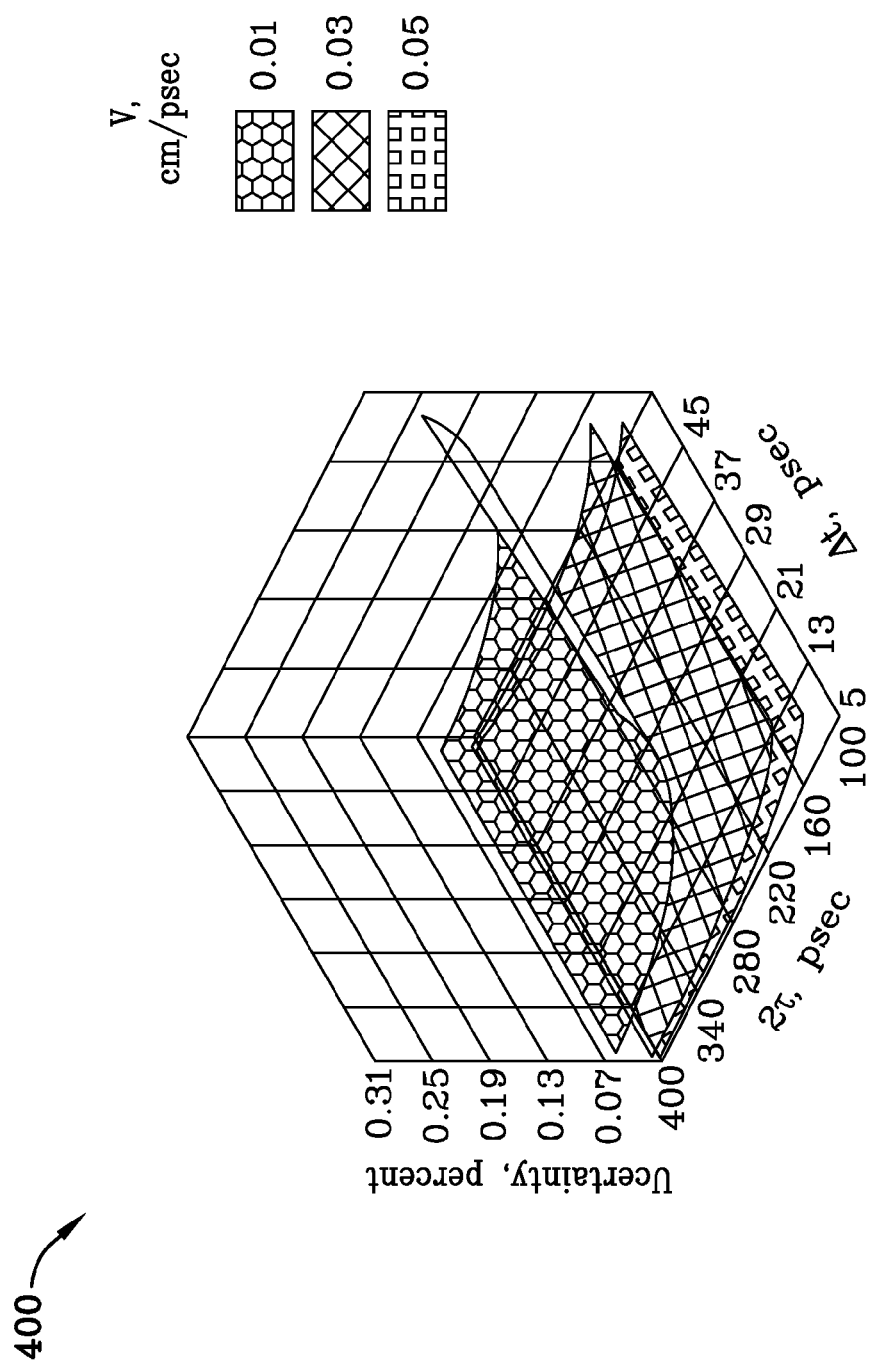
FIG. 4 is the uncertainty (in percentage) of the velocity (independent of the thickness) as a function of velocity, $2\tau$ and $\Delta t$.

FIG. 4 is a graph 400 of the uncertainty (in percentage) of the velocity (independent of the thickness) as a function of V (terahertz velocity in the material), $2\tau$ and $\Delta t$. The precision (uncertainty) in the thickness-independent velocity due to the random errors in the measurements of the variables $\Delta t$ and $2\tau$ was determined by the above equations and standard variance relation. Uncertainty in c was ignored and using typical values of $\Delta t \approx 6$ psec, $2\tau \approx 200$ psec, Sampling Rate=6.4 THz, c=0.02997055434 cm/psec, and V≈0.0290 cm/psec, gives Uv≈0.01 percent (uncertainty of the velocity in percent). FIG. 4 illustrates uncertainties (in percent) for three velocities, V, 0.01 cm/psec; 0.03 cm/psec; and, 0.05 em/psec.

Figure 5:
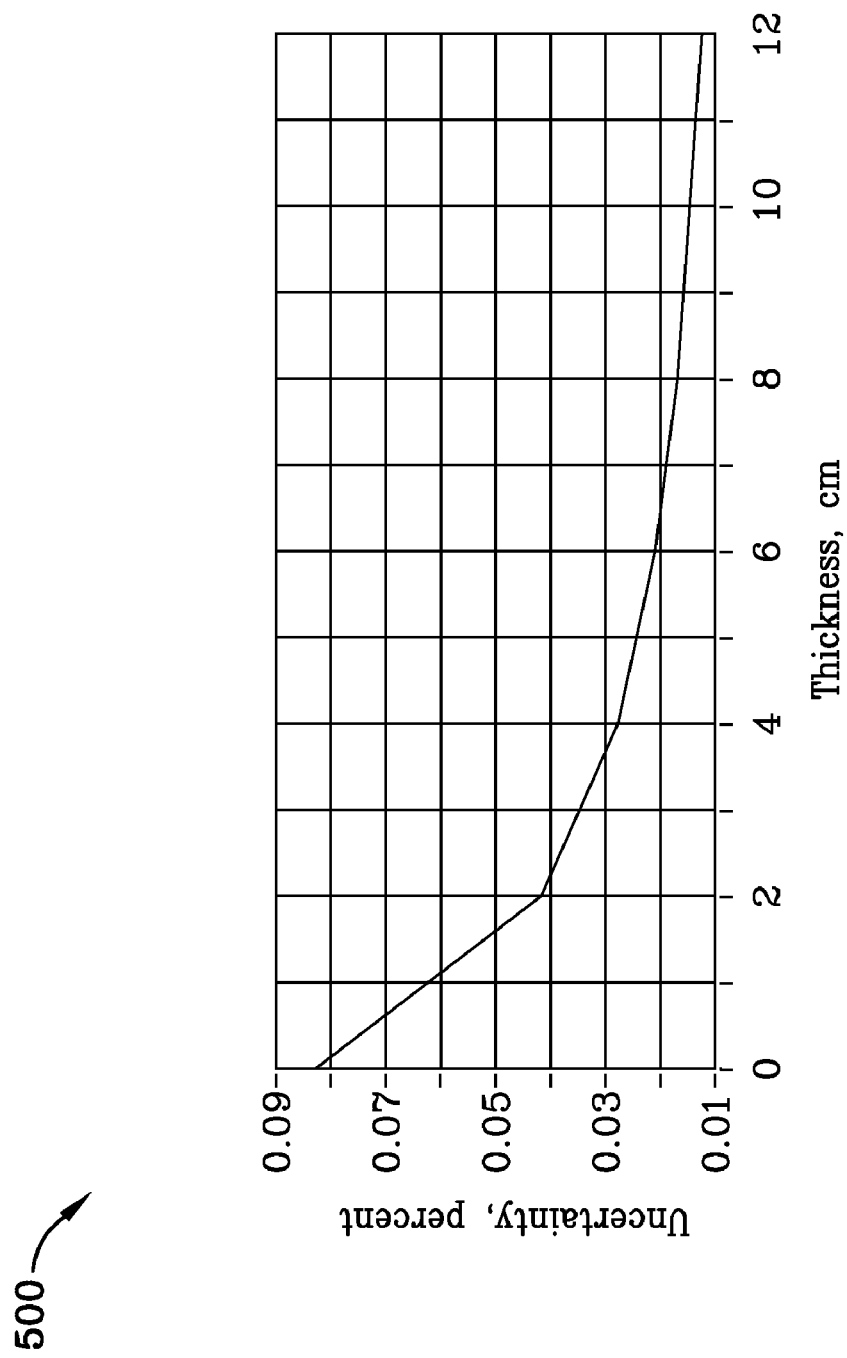
FIG. 5 is the uncertainty (in percentage) of the thickness (independent of the microstructural variations) as a function of thickness.

FIG. 5 is a graph 500 of the uncertainty (in percentage) of the thickness (independent of the microstructural variations) as a function of thickness, d. Similarly, the precision (uncertainty), Ud, of the thickness measurement is a function of the thickness as illustrated in FIG. 5. For the foam samples studied, and using typical values for SR=6.4 THz, c=0.02997055334 cm/psec, and thicknesses of approximately 3 to 5 cm, Ud=0.035 to 0.025 percent (uncertainty of the thickness in percent).

Figure 6:
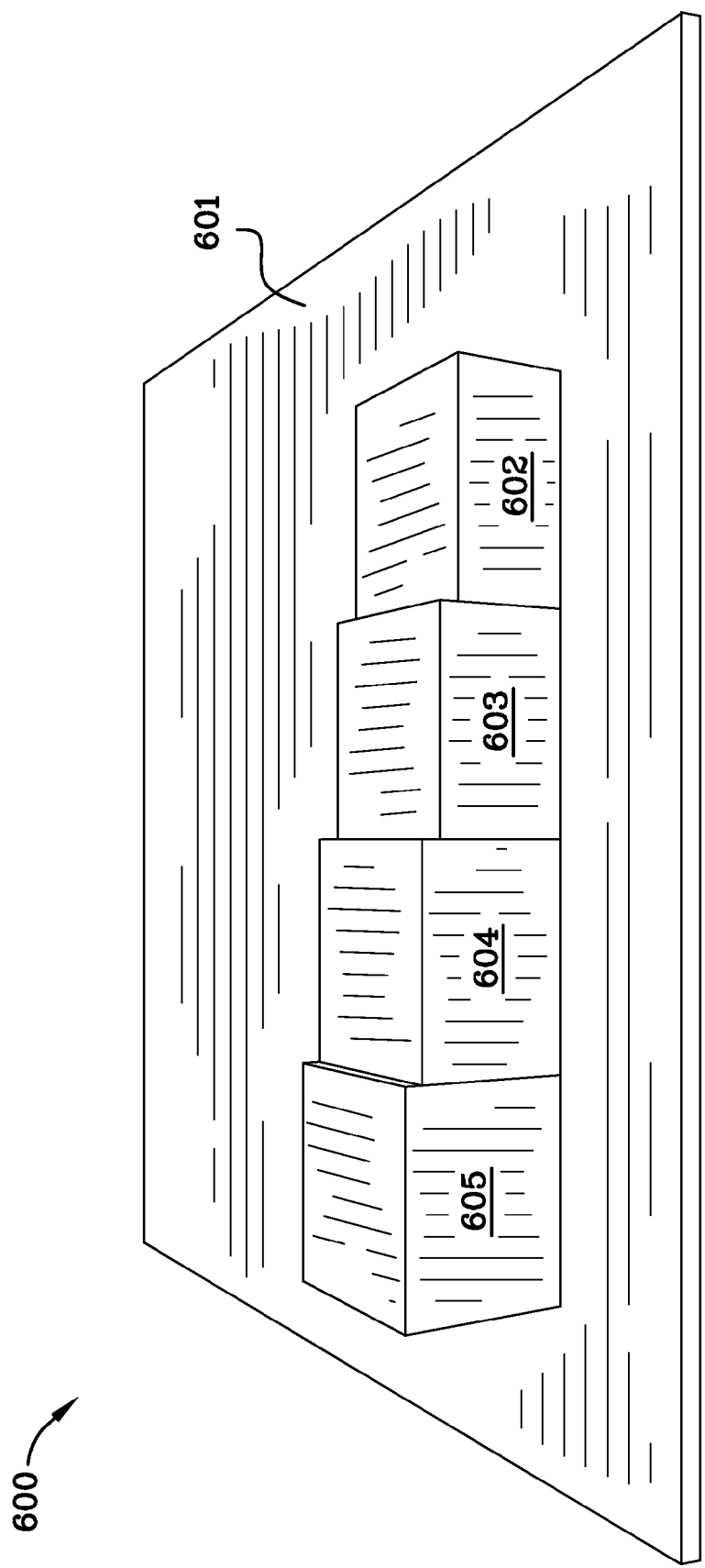
FIG. 6 is a perspective view of a foam block sample set on an aluminum plate.

FIG. 6 is a perspective view 600 of a foam block step wedge sample set on an aluminum plate 601. The first foam block 602, the second foam block 603, the third foam block 604, and the fourth foam block 605 are illustrated and arranged with increasing thickness and density from left to right. The foam block configuration of FIG. 6 is ordered as step wedges such that density and thickness variation results in an additive effect on 2τ.

FIG. 7 illustrates a composite image 700 of scans of the foam block sample set of FIG. 6 indicating 2τ values of the foam blocks according to the methodology of the invention as a function of thickness and density. FIG. 7 shows 2τ, FIG. 7A shows microstructure-independent thickness image and FIG. 7B shows thickness-independent density image for the foam blocks of FIG. 6, using the novel terahertz method described in this invention. The density image was derived from thickness-independent velocity images using the relationship between terahertz velocity and density for foam shown in FIG. 2. This sample has well-defined thickness and density variation that have additive effects on the 2τ image. It can be seen that the method is able to separate the thickness and density variation components as illustrated in FIGS. 7A and 7B.

FIG. 7A illustrates an image 700A of scans of the foam block sample set of FIG. 6 indicating thickness variations according to the methodology of the invention. FIG. 7B illustrates an image 700B of scans of the foam block sample set of FIG. 6 indicating density variations according to the methodology of the invention. The method of this invention separates thickness and density effects on time delay (2τ) between FS and BS echos. Increasing thickness and increasing density from right-to-left in the blocks of FIG. 6 provides an additive effect in terms of increasing 2τ from right-to-left. Scan and/or analog-to-digital conversion jitter (zigzag gray level pattern) is apparent in the density image of FIG. 7B. The terahertz experimental setup used in connection with the foam blocks of FIG. 6 was a broadband 1 THz scan system and included the following experimental and signal processing parameters:

Focus: (At substrate, or 3 cm above substrate for wedge samples)
Typical received bandwidth points (THz) (Full Width Half Max)≈0.1 to 0.3
Data Acquisition Rate (THz): 6.4
Waveform Length Acquired (psec/points): 320 psec/2048 points
Waveform Acquisition Rate (scan points/sec):≈10
Collinear source-detector: Yes
Spatial Resolution (at Full Width Half Max of Point Spread Function): 0.5 cm
Signal Acquisition Width of dynamic (peak-centered) gates for time delay computations (psec): 25 to 100 psec
Scan Increment (cm): 0.2

Samples were placed on an aluminum plate as shown in FIG. 6 and scanned with scan increments in the X and Y direction of 0.2 cm. The minimum number of scans required to obtain thickness-independent velocity and microstructure-independent thickness is two. One scan obtains FS and BS echos (with sample present) and the second scan obtains the M" echo (without sample present). Separate scans for FS and BS can be performed if sample thickness is too large to allow simultaneous capture of both of the echos in the 320 psec/2048 point window using the 6.4 THz sampling rate. Only two scans were required when the thicknesses were 4 cm and FS and BS could be captured in one scan. For each sample set, the scans were then fused (combined using software) such that FS, BS and M" echos were placed in a single wavetrain of 640 psec/4096 points length with time relationships between the echos preserved. This occurs at each scan location to create the new fused data set. Precise time delays 2τ and Δt were determined using cross-correlation between the echos' waveforms. Phase relationships were examined for: (1) FS compared to BS; and, (2) BS compared to M". All waves appeared to be in phase for the analysis made. If echos are in-phase with respect to each other, the time occurrence of the maximum in the correlation function was used to calculate time delay. If the echos were phase-inverted, the time occurrence of the minimum in the correlation function should be used to calculate time delays.

Figure 15:
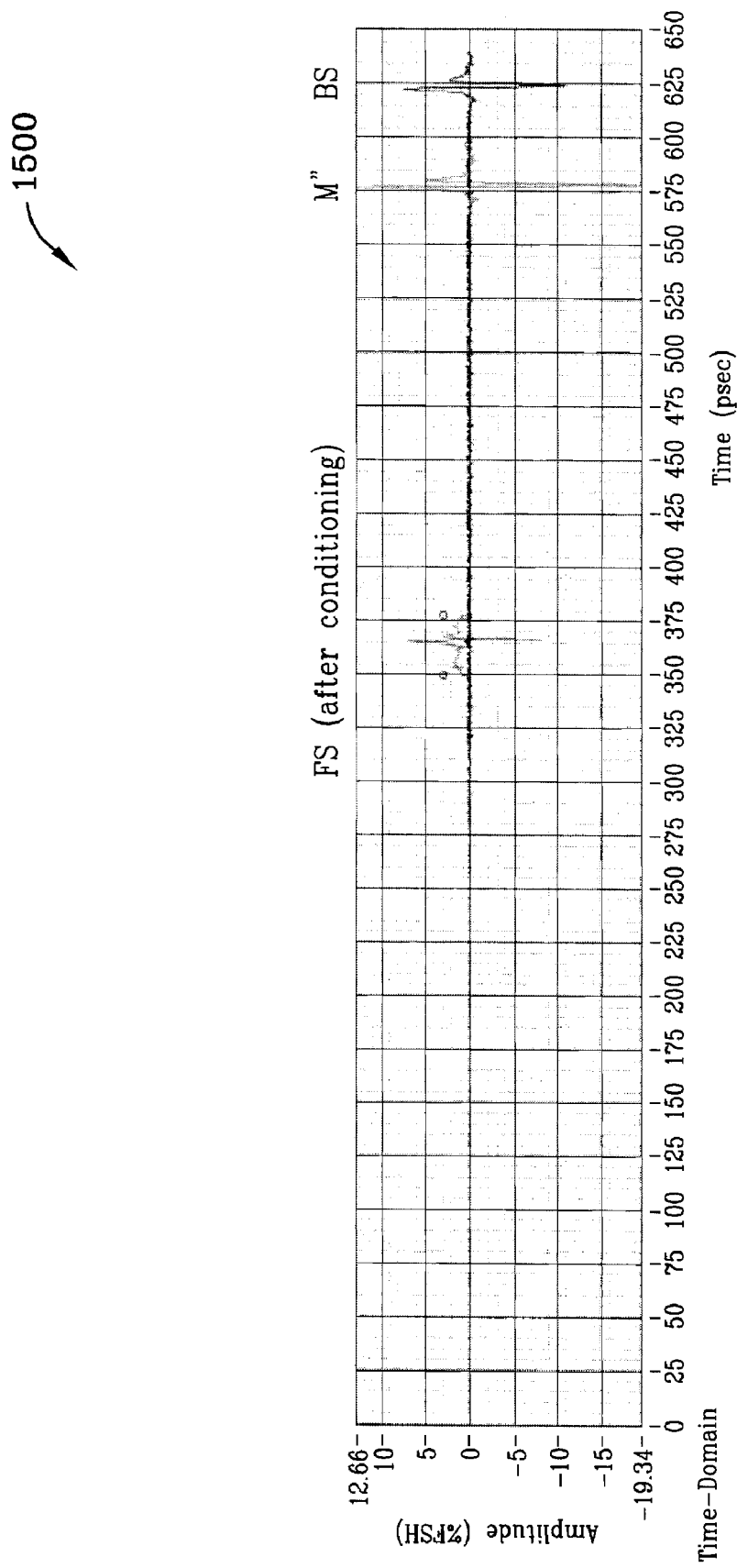
FIG. 15 is a typical "fused" waveform from a "fused" data file produced by merging the FS, BS, and M" scan data sets for a set of foam blocks.

A typical "fused" waveform from a "fused" data file is illustrated in FIG. 15. FIG. 15 is a typical "fused" waveform 1500 from a "fused" data file produced by merging the FS, BS, and M" scan data sets for a set of foam blocks.

The fused data file is produced by merging the FS, BS, and M" scan data sets for foam block sets. FS and BS occur with the sample present. M" occurs without the sample present. For visualization purposes, M" has been artificially shifted to the left an additional 40 psec in FIG. 15 to avoid overlap between the echoes. FS has been denoised, amplified, and a DC component has been subtracted therefrom so as to allow 2τ time delay calculation. A 25 to 100 psec gate (window) was applied to account for variations in FS echo position due to thickness variations in the sample. The gated region containing the FS echo was denoised using a wavelet process, then amplified by 10 to 40×, followed by subtraction of the DC component. The denoising process used the debauchies 05 mother wavelet principle. The resultant FS echo was quite useable as shown in FIG. 15. Two Tau (2t) and Δt are determined using the fusing process and the entire waveforms are either cross-correlated or the peaks are precisely identified enabling the measurement of the time between them. A computer process with an appropriate algorithm is used to calculate 2τ and Δt.

Figure 16:
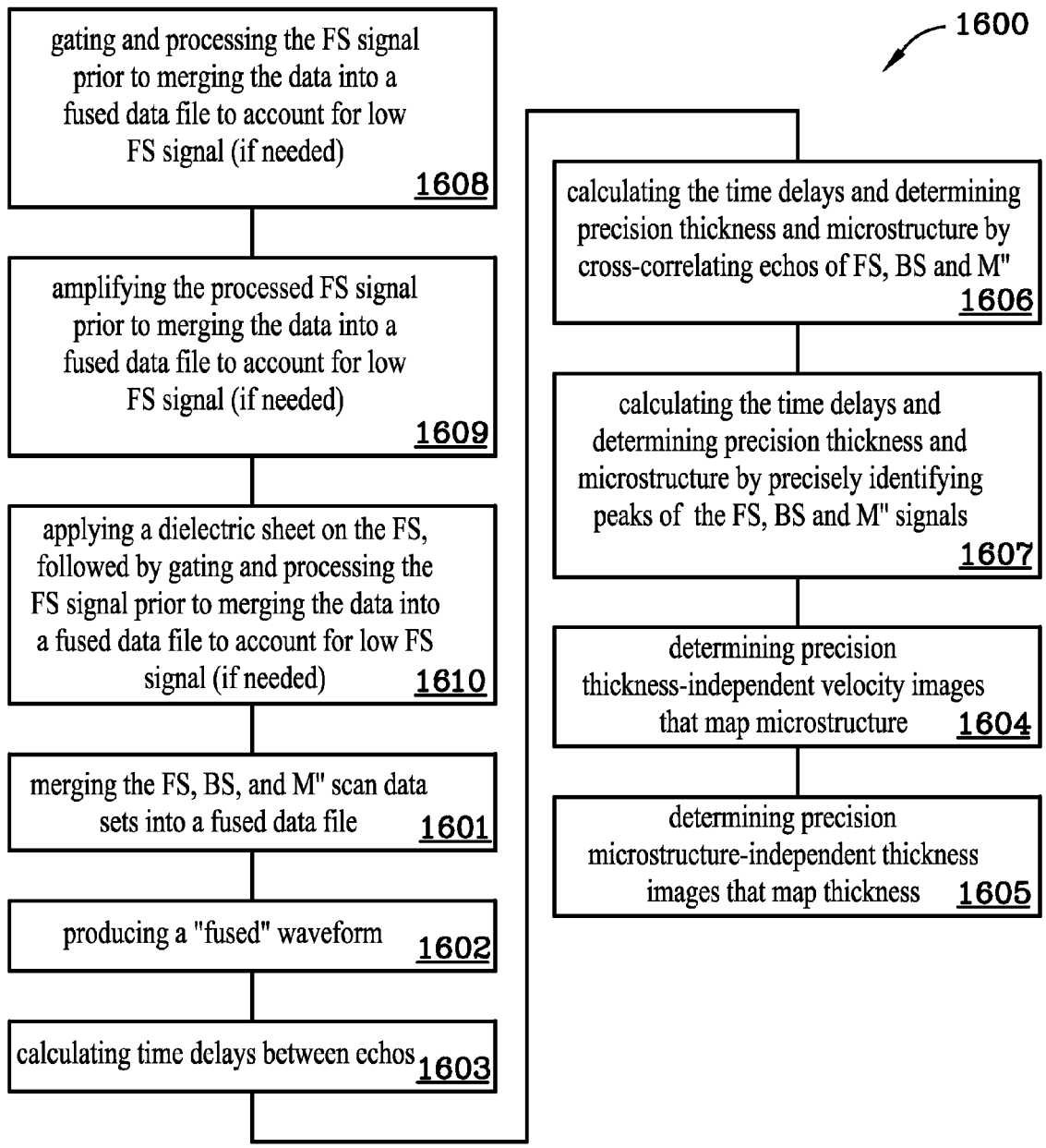
FIG. 16 is a schematic of a process (another example) for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample, the sample residing on a substrate.

FIG. 16 is a schematic 1600 of another process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample. The process includes the steps of: merging the FS, BS, and M" scan data sets into a fused data file 1601; producing a "fused" waveform 1602; calculating time delays between echos 1603; determining precision thickness-independent velocity images that map microstructure 1604; and, determining precision microstructure-independent thickness images that map thickness 1605. The steps of calculating the time delays and determining precision thickness and microstructure are performed by the step of cross-correlating the entire waveform of FS, BS and M" 1606. Alternatively, the steps of calculating the time delays and determining precision thickness and microstructure are performed by precisely identifying peaks of FS, BS and M" signals 1607.

If a poor dielectric mismatch occurs between the air and the sample, the step of gating and processing the FS signal prior to merging the data into a fused data file 1608 is performed. If the signal to noise ratio is low then the step of amplifying the processed FS signal prior to merging the data into a fused data file 1609 is performed. Further the step of applying a dielectric sheet on the FS, followed by gating and processing the FS signal prior to merging the data into a fused data file 1610 may optionally be performed to enhance the signal processing.

FIG. 8 illustrates 800 a physically-measured density map in grams per cubic centimeters for a 6 by 15 set of foam blocks with non regular thickness and density. The set of 6 by 15 foam blocks had dimensions of about 5 by 5 by 5 cm, with minor but non regular thickness variation (±0.1 cm). The blocks were of various densities ranging from about 0.042 to 0.054 g/cm$^3$ "(on the order of 20 percent)" measured from mass and dimensional measurements and were arranged randomly. FIG. 8A illustrates 800A the density by shade of gray in grams per cubic centimeter for the physically-measured density map shown in FIG. 8. FIG. 9 illustrates a terahertz density map 900 for the same 6 by 15 set of foam blocks derived from the velocity variations (determined independently of thickness) according to the methodology of the invention using the relationship between terahertz velocity and density for foam shown in FIG. 2. FIG. 9A illustrates 900A the density by shade of gray in grams per cubic centimeter for the derived terahertz density map shown in FIG. 9.

Reference numeral 801 represents an area of the physically measured density map and reference numeral 901 represents an area of the mapped terahertz density plot for the same set of foam blocks. Reference numeral 802 represents an area of the physically-measured density shown in FIG. 8 of the set of foam blocks and reference numeral 902 represents an area of the mapped terahertz density plot for the same set of foam blocks. Viewing lighter and darker areas (801, 901, 802, 902) in the images of FIGS. 8 and 9, it is clear that the physically-measured density variation agrees quite closely with that derived from the thickness-independent velocity.

FIG. 10 illustrates a hand-measured thickness map 1000 in centimeters for the same 6 by 15 set of foam blocks. FIG. 11 illustrates a terahertz thickness image 1100 for the 6 by 15 set of foam blocks (determined independently of velocity) according to the methodology of the invention. FIG. 10A illustrates the thickness in centimeters by shade of gray in a bar graph 1000A. FIG. 11A illustrates the thickness 1100A by shade of gray in centimeters for the terahertz thickness map of FIG. 11. As stated previously the blocks vary in thickness from 5 cm by ±0.1 cm. Reference numeral 1001 is an ellipse indicating an area of the hand measured thickness map to be compared to a terahertz thickness map and reference numeral 1101 is an ellipse indicating an area of the terahertz thickness map to be compared to a physically measured thickness map. Note the excellent correlation between dark and light areas in both images. Ellipses 1001 and 1101 denote the identical area under examination. Good correlation within ellipses 1001 and 1101 between light and dark areas is observable. Dark scatter spots in the terahertz generated thickness are due to the presence of an additional echo within the signal processing gate that results in improper cross-correlation delay calculation. This additional echo is likely due to the presence of extra material on the surface. These scatter spots are also in the thickness-independent velocity image of FIG. 9 but blend in better as they cause variation in that image in the same "direction" as actual velocity variations.

Figure 12:
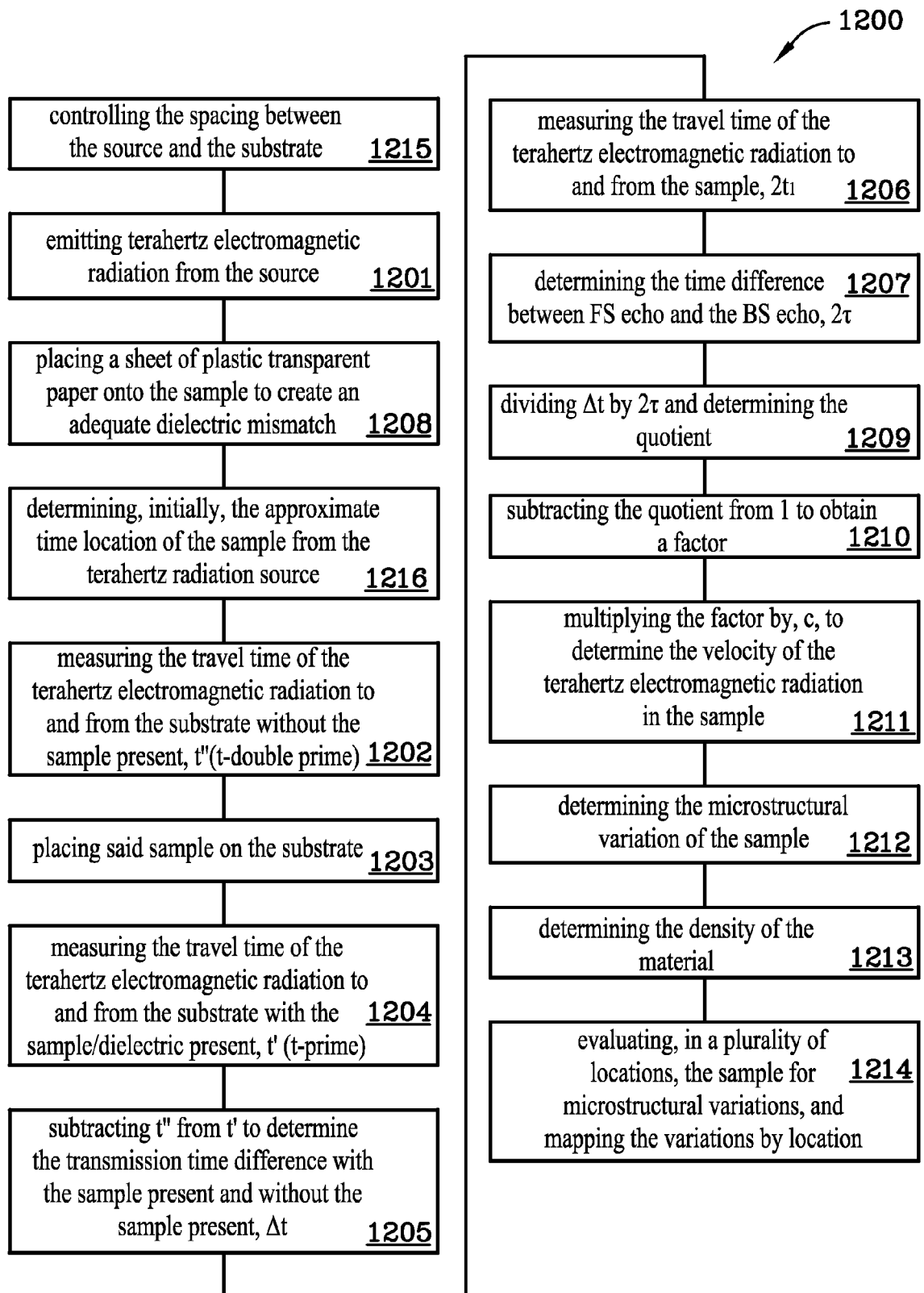
FIG. 12 is a schematic diagram of a process for measuring the velocity of terahertz electromagnetic radiation in a material sample without prior knowledge of the thickness of the sample, the terahertz electromagnetic radiation produced by a source (transceiver) spaced apart from the sample under test and propagated at the speed of light, c, in a medium located between the source (transceiver) and the sample, the sample residing on a substrate.

FIG. 12 is a schematic diagram 1200 of a process for measuring the velocity of terahertz electromagnetic radiation in a material sample without prior knowledge of the thickness of the sample, the terahertz electromagnetic radiation produced by a source (transceiver) spaced apart from the sample under test and propagated at the speed of light, c, in a medium located between the source and the sample. The steps of the process may be performed in any desired or necessary order. The process includes the steps of: emitting pulsed terahertz electromagnetic radiation from the source 1201 (the radiation may be pulsed or it may be continuous); measuring the travel time of the terahertz electromagnetic radiation to and from the substrate without the sample present, t" (t-double prime), 1202; placing the sample on the substrate 1203; measuring the travel time of the terahertz electromagnetic radiation to and from the substrate with the sample/dielectric present, t' (t-prime) 1204; subtracting t" from t' to determine the transmission time difference with the sample present and without the sample present, Δt, 1205; measuring the travel time of the terahertz electromagnetic radiation to and from the sample, $2t_1$, 1206; determining the time difference between the FS echo and the BS echo, 2τ, 1207; placing a sheet of plastic transparent paper onto the sample to create an adequate dielectric mismatch 1208; dividing Δt by 2τ and determining the quotient 1209; subtracting the quotient from 1 to obtain a factor 1210; multiplying the factor by, c, to determine the velocity of the terahertz electromagnetic radiation in the sample 1211; determining the microstructural variation of the sample 1212; determining the density of the material 1213; evaluating, in a plurality of locations, the sample for microstructural variations; and mapping the variations by location 1214; controlling the spacing between the source and the substrate 1215; and, determining, initially, the approximate time location of the sample from the terahertz radiation source 1216. Additionally, the step of determining the microstructual variation of the sample may include the determination of a parameter other than density. In the case of a poor dielectric mismatch between the air and the sample to be inspected, the process can include a step of placing a sheet of plastic transparent paper onto said sample to create an adequate dielectric mismatch.

Figure 13:
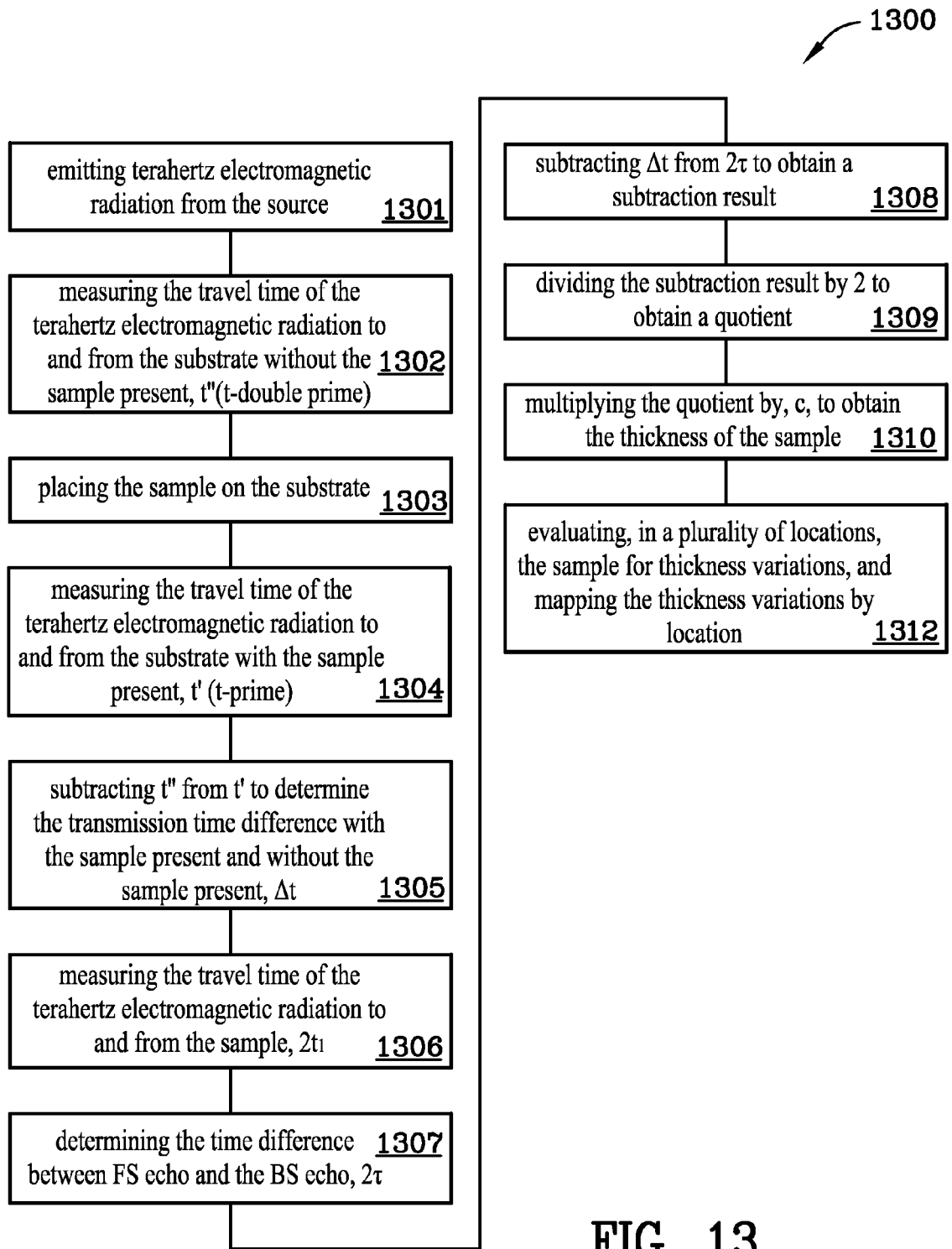
FIG. 13 is a schematic diagram of a process for measuring the thickness of a material sample using terahertz electromagnetic radiation in a material sample without prior knowledge of the velocity of the terahertz electromagnetic radiation in the sample, the terahertz electromagnetic radiation produced by a source (transceiver) spaced apart from the sample under test and propagated at the speed of light, c, in a medium located between the source (transceiver) and the sample, the sample residing on a substrate.

FIG. 13 is a schematic diagram 1300 of a process for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample. The process for measuring the thickness using terahertz electromagnetic radiation includes: emitting terahertz electromagnetic radiation from the source 1301 (the radiation may be pulsed or it may be continuous); measuring the travel time of the terahertz electromagnetic radiation to and from the substrate without the sample present, t" (t-prime), 1302; placing the sample on the substrate 1303; measuring the travel time of the terahertz electromagnetic radiation to and from the substrate with the sample present, t'(t-prime), 1304; subtracting t" from t' to determine the transmission time difference with the sample present and without the sample present, Δt, 1305; measuring the travel time of the terahertz electromagnetic radiation to and from the sample, $2t_1$, 1306; determining the time difference between the FS echo and the BS echo, 2τ, 1307; subtracting Δt from 2τ to obtain a subtraction result 1308; dividing the subtraction result by 2 to obtain a quotient 1309; multiplying the quotient by, c, to obtain the thickness of the sample 1310; and, evaluating, in a plurality of locations, the sample for thickness variations; and mapping the thickness variations by location 1312.

Figure 14:
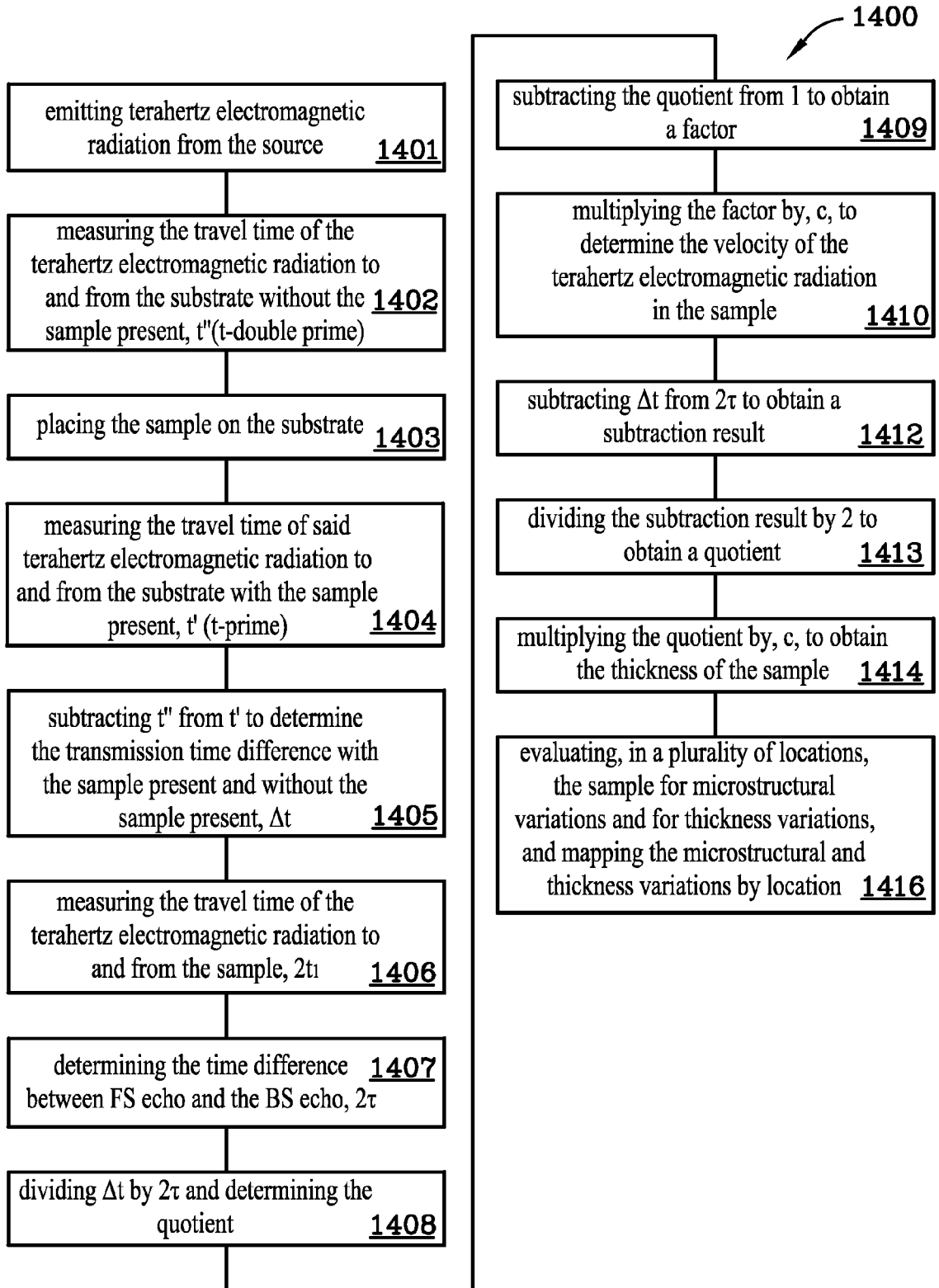
FIG. 14 is a schematic of a process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source (transceiver) spaced apart from the sample under test and propagated at the speed of light, c, in a medium located between the source (transceiver) and the sample, the sample residing on a substrate.

FIG. 14 is a schematic 1400 of a process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample. The process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample includes the steps of: emitting terahertz electromagnetic radiation from the source 1401 (the radiation may be pulsed or it may be continuous); measuring the travel time of the terahertz electromagnetic radiation to and from the substrate without the sample present, t" (t-double prime) 1402; placing the sample on the substrate 1403; measuring the travel time of the terahertz electromagnetic radiation to and from the substrate with the sample present, t' (t-prime) 1404; subtracting t" from t' to determine the transmission time difference with the sample present and without the sample present, Δt, 1405; measuring the travel time of the terahertz electromagnetic radiation to and from the sample, $2t_1$, 1406; determining the time difference between the FS echo and the BS echo, 2τ, 1407; dividing Δt by 2τ and determining the quotient 1408; subtracting the quotient from 1 to obtain a factor 1409; multiplying the factor by, c, to determine the velocity of the terahertz electromagnetic radiation in the sample 1410; subtracting Δt from 2τ to obtain a subtraction result 1412; dividing the subtraction result by 2 to obtain a quotient 1413; multiplying the quotient by, c, to obtain the thickness of the sample 1414; and, evaluating, in a plurality of locations, the sample for microstructural variations and for thickness variations, and mapping the microstructural and thickness variations by location 1416.

REFERENCE NUMERALS

100—schematic view of the terahertz measuring system
101—transceiver
102—terahertz source
103—terahertz receiver
104—front surface of metal substrate
104A—metal substrate
105—back surface of metal substrate
106—beginning of void
107—end of void/front surface of metal substrate
108—foam, silicon nitride or other dielectric
109—front surface of foam, silicon nitride or other dielectric
110—gate for signal analysis
200—density of sprayed on foam insulation versus velocity of terahertz electromagnetic radiation therein
200A—density of silicon nitride versus velocity of terahertz electromagnetic radiation therein
300—schematic view of terahertz measuring system and graph of output voltages of respective signals versus time
301—thin dielectric sheet
400—graph of uncertainty (in percent) of thickness independent velocities as a function of 2τ, Δt and V.
500—graph of uncertainty (in percent) of velocity as a function of thickness, d.
600—schematic of step wedge foam blocks
601—aluminum substrate
602—first foam block
603—second foam block
604—third foam block
605—fourth foam block
700—plot of 2τ as a function of thickness and density
700A—schematic illustration of thickness variation
700B—schematic illustration of density variation
800—physically measured density map for a 6 by 15 set of foam blocks
800A—density plot
801—comparison portion of physically measured density map
802—comparison portion of physically measured density map
900—terahertz density map
900A—terahertz density plot
901—comparison portion of thickness independent terahertz density map
902—comparison portion of thickness independent terahertz density map
1000—hand measured thickness map for a 6 by 15 set of foam blocks
1000A—illustrates the thickness in centimeters by shade of gray
1001—ellipse indicating an area of the hand measured thickness map to be compared to a terahertz thickness map
1100—a terahertz thickness image for the 6 by 15 set of foam blocks (determined independently of velocity) according to the methodology of the invention
1100A—thickness by shade of gray in centimeters for the terahertz thickness map of FIG. 11
1101—ellipse indicating an area of the terahertz thickness map to be compared to a physically measured thickness map
1200—schematic diagram of a process for measuring the velocity of terahertz electromagnetic radiation in a material sample without prior knowledge of the thickness of the sample, the terahertz electromagnetic radiation produced by a source spaced apart from the sample under test at the speed of light, c, in a medium located between the source and the sample, the sample residing on the substrate
1201—emitting terahertz electromagnetic radiation from the source
1202—measuring the travel time of the terahertz electromagnetic radiation to and from the substrate without the sample present, t" (t-double prime)
1203—placing the sample on the substrate
1204—measuring the travel time of the terahertz electromagnetic radiation to and from the substrate with the sample/dielectric present, t' (t-prime)
1205—subtracting t" from t' to determine the transmission time difference with the sample present and without the sample present, Δt
1206—measuring the travel time of the terahertz electromagnetic radiation to and from the sample, $2t_1$
1207—determining the time difference between the FS echo and the BS echo, 2τ
1208—placing a sheet of plastic paper onto the sample to create an adequate dielectric mismatch
1209—dividing Δt by 2τ and determining the quotient
1210—subtracting the quotient from 1 to obtain a factor
1211—multiplying the factor to determine the velocity of the terahertz electromagnetic radiation in the sample
1212—determining the microstructural variation of the sample
1213—determining the density of the material
1214—evaluating, in a plurality of locations, the sample for microstructural variations; and mapping the variations by location
1215—controlling the spacing between the source and the substrate
1216—determining, initially, the approximate time location of the sample from the terahertz radiation source
1300—schematic diagram of a process for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample, the sample residing on the substrate 1301—emitting terahertz electromagnetic radiation from the source;

1302—measuring the travel time of the terahertz electromagnetic radiation to and from the substrate without the sample present, t"(t-double prime)

1303—placing the sample on the substrate

1304—measuring the travel time of the terahertz electromagnetic radiation to and from the substrate with the sample present, t' (t-prime)

1305—subtracting t" from t' to determine the transmission time difference with the sample present and without the sample present, $\Delta t$ 1306—measuring the travel time of the terahertz electromagnetic radiation to and from the sample, $2t_1$ 1307—determining the time difference between the FS echo and the BS echo, $2\tau$ 1308—subtracting $\Delta t$ from $2\tau$ to obtain a subtraction result 1309—dividing the subtraction result by 2 to obtain a quotient 1310—multiplying the quotient by, c, to obtain the thickness of the sample 1312—evaluating, in a plurality of locations, the sample for thickness variations; and mapping the thickness variations by location 1400—schematic diagram of a process for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the sample under test and propagated at the speed of light, c, in a medium located between the source and the sample under test, the sample residing on the substrate 1401—emitting terahertz electromagnetic radiation from the source 1402—measuring the travel time of the terahertz electromagnetic radiation to and from the substrate with the sample present, t' (t-prime)

1403—placing the sample on the substrate

1404—measuring the travel time of the terahertz electromagnetic radiation to and from the substrate without the sample present, t" (t-double prime)

1405—subtracting t" from t' to determine the transmission time difference with the sample present and without the sample present, $\Delta t$ 1406—measuring the travel time of the terahertz electromagnetic radiation to and from the sample, $2t_1$ 1407—determining the time difference between the FS echo and the BS echo, $2\tau$ 1408—dividing $\Delta t$ by $2\tau$ and determining the quotient 1409—subtracting the quotient from 1 to obtain a factor 1410—multiplying the factor to determine the velocity of the terahertz electromagnetic radiation in the sample 1412—subtracting $\Delta t$ from $2\tau$ to obtain a subtraction result 1413—dividing the subtraction result by 2 to obtain a quotient 1414—multiplying the quotient by, c, to obtain the thickness of the sample 1416—evaluating, in a plurality of locations, the sample for microstructural variations and for thickness variations, and mapping the microstructural and thickness variations by location.

1500—fused waveform from a "fused" data file produced by merging the FS, BS, and M" scan data sets for a set of foam blocks.

1600—another process for simultaneously measuring the velocity of terahertz electromagnetic radiation in a material sample without prior knowledge of the thickness of the sample and for measuring the thickness of a material sample using terahertz electromagnetic radiation in a material sample without prior knowledge of the velocity of the terahertz electromagnetic radiation in the sample, the terahertz electromagnetic radiation produced by a source spaced apart from the substrate and propagated at the speed of light, c, in a medium located between the source and the substrate.

1601—merging the FS, BS, and M" scan data sets into a fused data file.

1602—producing a "fused" waveform 1602.

1603—calculating time delays between echos.

1604—determining precision thickness-independent velocity images that map microstructure.

1605—determining precision microstructure-independent thickness images that map thickness.

1606—calculating the time delays and determining precision thickness and microstructure are performed by the step of cross-correlating entire waveforms FS, BS and M".

1607—calculating the time delays and determining precision thickness and microstructure are performed by precisely identifying peaks of FS, BS and M" signals.

1608—gating and processing the FS signal prior to merging the data into a fused data file to account for low FS signal (if needed)

1609—amplifying the processed FS signal prior to merging the data into a fused data file to account for FS signal (if needed)

1610—applying a dielectric sheet on the front surface, followed by processing and gating the FS signal prior to merging the data into a fused data file to account for low FS signal (if needed)

BS—pulse that travels from the transceiver to the reflector plate and back to the transceiver with the sample present FS—pulse that travels from the transceiver to the front surface of the sample and back to the transceiver L—distance between transceiver and sample M"—pulse that travels from the transceiver to the reflector plate and back to the transceiver without the sample present c—speed of light in a medium located between the source of the terahertz radiation and the substrate d—sample thickness t' (t-prime)—travel time of the terahertz electromagnetic radiation to and from the substrate with the sample present;

t" (t-double prime)—travel time of the terahertz electromagnetic radiation to and from the substrate without the sample present;

$\Delta t$—transmission time difference (t' minus t") with the sample present and without the sample present;

$2t_1$—measuring the travel time of the terahertz electromagnetic radiation to and from the sample;

$2\tau$—time difference between the FS echo and the BS echo, $2\tau$

V—velocity

Those skilled in the art will readily recognize that the invention has been set forth by way of example only. Accordingly, those skilled in the art will recognize that changes may be made to the invention without departing from the spirit and scope of the attached claims.

The invention claimed is:

1. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, comprising the steps of:
- emitting terahertz electromagnetic radiation from said source;
- measuring the travel time of said terahertz electromagnetic radiation to and from said substrate without said sample present, t";
- placing said sample on said substrate;
- measuring the travel time of said terahertz electromagnetic radiation to and from said substrate with the sample present, t';
- subtracting t" from t' to determine the transmission time difference with said sample present and without said sample present, $\Delta t$;
- measuring the travel time of said terahertz electromagnetic radiation to and from said sample, $2t_1$;
- determining the time difference between t' and the $2t_1$, $2\tau$;
- dividing $\Delta t$ by $2\tau$ and determining the quotient;
- subtracting said quotient from 1 to obtain a factor; and
- multiplying said factor by, c, to determine the velocity of said terahertz electromagnetic radiation in said sample.

2. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 1 wherein said emission of said terahertz electromagnetic radiation is continuous.

3. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 1 wherein said emission of said terahertz electromagnetic radiation is pulsed.

4. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 3 further comprising the step of:
- determining the microstructural variation of said sample.

5. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 4 wherein said step of determining the microstructural variation of said sample includes determining the density of the material.

6. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 5 wherein said sample is a dielectric.

7. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 4 wherein said sample is foam.

8. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 4 wherein said sample is a dielectric.

9. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 4, further comprising the steps of:
- evaluating, in a plurality of locations, said sample for microstructural variations; and mapping said variations by location.

10. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 3 wherein said sample is foam.

11. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 10 wherein said sample is foam.

12. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 3 wherein said sample is a dielectric.

13. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 3 wherein the step of measuring the travel time of said terahertz electromagnetic radiation to and from said sample, $2t_1$ includes placing a sheet of plastic paper onto said sample to create an adequate dielectric mismatch.

14. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 13 wherein said sheet of plastic paper is less than or equal to 250 µm thick.

15. A process for measuring the thickness of a material sample using terahertz electromagnetic radiation in a material sample without prior knowledge of the velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 13, further comprising the steps of:
   evaluating, in a plurality of locations, said sample for thickness variations; and mapping said thickness variations by location.

16. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 3, further comprising the step of controlling said spacing between said source (transceiver) and said sample.

17. A process for measuring the velocity of terahertz electromagnetic radiation in a material sample without prior knowledge of the thickness of said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 3, wherein said step of controlling said spacing between said source (transceiver) and said sample under test includes determining, initially, the approximate time location of said sample from said terahertz radiation source.

18. A process for measuring the thickness of a material using terahertz electromagnetic radiation in a material sample without prior knowledge of the velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, comprising the steps of:
   emitting terahertz electromagnetic radiation from said source;
   measuring the travel time of said terahertz electromagnetic radiation to and from said substrate without said sample present, t";
   placing said sample on said substrate;
   measuring the travel time of said terahertz electromagnetic radiation to and from said substrate with said sample present, t';
   subtracting t" from t' to determine the transmission time difference with said sample present and without said sample present, $\Delta t$;
   measuring the travel time of said terahertz electromagnetic radiation to and from said sample, $2t_1$;
   determining the time difference between t' and $2t_1$, $2\tau$;
   subtracting $\Delta t$ from $2\tau$ to obtain a subtraction result;
   dividing said subtraction result by 2 to obtain a quotient;
   multiplying said quotient by, c, to obtain the thickness of said sample; and,
   determining the thickness of the sample.

19. A process for simultaneously measuring the velocity of terahertz electromagnetic radiation in a material sample without prior knowledge of the thickness of said sample and for measuring the thickness of a material sample using terahertz electromagnetic radiation in a material sample without prior knowledge of the velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, said sample residing on a substrate, comprising the steps of:
   emitting terahertz electromagnetic radiation from said source;
   measuring the travel time of said terahertz electromagnetic radiation to and from said substrate without said sample present, t";
   placing said sample on said substrate;
   measuring the travel time of said terahertz electromagnetic radiation to and from said substrate with said sample present, t';
   subtracting t" from t' to determine the transmission time difference with said sample present and without said sample present, $\Delta t$;
   measuring the travel time of said terahertz radiation to and from said sample, $2t_1$;
   determining the time difference between t' and $2t_1$, $2\tau$;
   dividing $\Delta t$ by $2\tau$ and determining the quotient;
   subtracting said quotient from 1 to obtain a factor;
   multiplying said factor by, c, to determine the velocity of said terahertz electromagnetic radiation in said sample;
   subtracting $\Delta t$ from $2\tau$ to obtain a subtraction result;
   dividing said subtraction result by 2 to obtain a quotient;
   multiplying said quotient by, c, to obtain the thickness of said sample;
   evaluating, in a plurality of locations, said sample for microstructural variations and for thickness variations, and mapping said microstructural and thickness variations by location.

20. A process for simultaneously measuring the velocity of terahertz electromagnetic radiation in a material sample without prior knowledge of the thickness of said sample and for measuring the thickness of a material sample using terahertz electromagnetic radiation in a material sample without prior knowledge of the velocity of said terahertz electromagnetic radiation in said sample, said terahertz electromagnetic radiation produced by a source, namely, a transceiver, spaced apart from said sample under test and propagated at the speed of light, c, in a medium located between said source, namely, said transceiver, and said sample, said sample residing on a substrate, as claimed in claim 19 wherein a sheet of plastic paper is utilized to determine the travel time of said terahertz radiation to and from said sample, $2t_1$.

* * * * *